United States Patent
Min et al.

(10) Patent No.: US 9,839,382 B2
(45) Date of Patent: Dec. 12, 2017

(54) DEVICE AND METHOD FOR SENSING BLOOD GLUCOSE

(71) Applicant: PACESETTER, INC., Sylmar, CA (US)

(72) Inventors: Xiaoyi Min, Camarillo, CA (US); Xi Lin Chen, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 119 days.

(21) Appl. No.: 14/715,385

(22) Filed: May 18, 2015

(65) Prior Publication Data
US 2016/0338624 A1 Nov. 24, 2016

(51) Int. Cl.
A61B 5/00 (2006.01)
A61B 5/1473 (2006.01)
A61B 5/145 (2006.01)

(52) U.S. Cl.
CPC ........ *A61B 5/1473* (2013.01); *A61B 5/14532* (2013.01); *A61B 5/686* (2013.01); *A61B 5/7278* (2013.01); *A61B 2560/0219* (2013.01)

(58) Field of Classification Search
CPC .......................... A61B 5/14532; A61B 5/1473
See application file for complete search history.

(56) References Cited

U.S. PATENT DOCUMENTS

| 6,014,029 A | 1/2000 | Soto et al. |
| 2013/0178751 A1 | 7/2013 | Min |
| 2014/0100627 A1 | 4/2014 | Min |
| 2014/0213916 A1 | 7/2014 | Doan |

OTHER PUBLICATIONS

Kim et al. "Rapid, Sensitive, and Reusable Detection of Glucose by a Robust Radiofrequency Integrated Passive Device Biosensor Chip". Jan. 15, 2015.*
Anoop Adhyapak, Analytical Model for Real Time, Noninvasive Estimation of Blood Glucose Level, 2014. (4 pages).
Tutku Karacolak, Cole-Cole Model for Glucose-Dependent Dielectric Properties of Blood Plasma for Continuous Glucose Monitoring, (4) pages, Department of Electrical and Computer Engineering.
A.S. Elwakil, B. Maundy; Extracting the Cole-Cole impedance model parameters without direct impedance measurement, Sep. 30, 2010 vol. 46 No. 20, (2 pages).

* cited by examiner

*Primary Examiner* — Christian Jang

(57) ABSTRACT

In accordance with one embodiment, a blood glucose sensing device is provided that comprises a house having of an exterior surface and that defines an interior space. The housing is configured to be located within a cardiovascular pathway of a patient. An inductor-capacitor (LC) circuit is located within the interior space defined by the housing. The inductor-capacitor circuit comprises an inductive circuit and a capacitive circuit electronically coupled to one another. The inductive and capacitive circuit has inductance and capacitance values that define a blood glucose sensitive resonant frequency such that a resonant frequency of the LC resonant circuit varies in response to changes in blood glucose levels within the blood in the cardiovascular pathway surrounding the housing.

17 Claims, 18 Drawing Sheets

DEVICE AND METHOD FOR SENSING BLOOD GLUCOSE

BACKGROUND OF THE INVENTION

Embodiments of the present disclosure generally relate to blood glucose and more particularly to methods and devices that utilize electromagnetic principles to detect changes in the transmembrane electrolyte balance due to glucose induced fluid shift.

Congestive heart failure (CHF) is emerging as a major public health concern, representing a significant cause of hospitalization for individuals aged 65 years and older. Two of the most prominent risk factors for heart failure are hypertension (high blood pressure) and diabetes. Not only do people with diabetes tend to have a cluster of risk factors for heart diseases, including hypertension, obesity, insulin resistance, and abnormal blood lipid levels, but diabetes itself is also an independent risk factor for the condition. People with diabetes are more likely to develop heart disease than the general population.

For people with diabetes, there is growing evidence that controlling blood glucose levels is very important in preventing heart disease. According to the American Diabetes Association, self-monitoring of blood glucose (SMBG) has a positive impact on the outcome of therapy and helps to achieve specific glycemic goals. However, the inconvenience, expense, pain, and complexity involved in invasive measurement methods commercially available lead to underutilization, mainly in people with type II diabetes.

Today, certain noninvasive (NI) methods have been proposed for determining blood glucose levels. The convention NI methods fall into two categories. The first category of methods is based on the measurement of glucose using one or more of the intrinsic molecular properties of glucose, such as the near-infrared or mid-infrared absorption coefficient, optical rotation, Raman shifts, and photo-acoustic absorption, as well as others. The second category of methods measures the effects of glucose on the physical properties of blood and tissue. The second category of methods is based on an assumption that glucose is a dominant (highly fluctuating) blood analyte and, as such, contributes significantly to the change in the relevant physical parameters of the tissue. Hence, measurement of such parameters can lead indirectly to evaluation of the blood glucose (BG) level. The measured parameters are evaluated relatively to calibration, performed through correlation of the NI signal to a reference BG value. Therefore, the relative change of glucose in blood or interstitial fluid (ISF) plays the major role, as other blood analytes, which are less fluctuating, are fully or at least partially eliminated through calibration.

However, conventional methods for measuring blood glucose experience certain limitations. For example, non-invasive methods may require a blood sample to be taken before testing and/or may be available only when the patient visits a doctor's office. For example, at least some conventional methods use external devices that have sensors attached to the skin. The skin sensors present the potential for variations in the sensor-skin interface, changes in micro-circulation, and metabolic rate etc. Those variables cause some challenges in measurement accuracy and sophisticated calibration is required for achieving required accuracy. Further, conventional methods may require the patient to take certain actions to perform the test at various times throughout the day.

A need remains for a blood glucose monitoring device and method that are accurate, painless, and easy-to-operate in order to encourage more frequent testing, leading to tighter glucose control and a delaying/decreasing of long-term complications and the associated health care costs.

SUMMARY

In accordance with one embodiment, a blood glucose sensing device is provided that comprises a house having of an exterior surface and that defines an interior space. The housing is configured to be located within a cardiovascular pathway of a patient. An inductor-capacitor (LC) circuit is located within the interior space defined by the housing. The inductor-capacitor circuit comprises an inductive circuit and a capacitive circuit electronically coupled to one another. The inductive and capacitive circuit has inductance and capacitance values that define a blood glucose sensitive resonant frequency such that a resonant frequency of the LC resonant circuit varies in response to changes in blood glucose levels within the blood in the cardiovascular pathway surrounding the housing.

Optionally, the device comprises a microprocessor that is configured to process signals received from the LC resonant circuit to generate date representative of the blood glucose level. The microprocessor may process the signals from the LC resonant circuit to determine the resonant frequency of the LC resonant circuit; and based on the resonant frequency, determines the blood glucose level. The device may comprise an implantable medical device (IMD) coupled to a proximal end of the lead, the IMD including the microprocessor, the lead having a distal end configured to be implanted within a heart of the patient, the LC resonant circuit located within the lead proximate to the distal end such that the LC resonant circuit is located within a chamber of the heart.

Optionally, the device further comprises a battery circuit, the LC resonant circuit further comprising an excitation circuit electrically coupled to receive power from the battery circuit and configured to excite the inductor-capacitor resonant circuit by generating an excitation signal. The LC resonant circuit is configured to be excited by an excitation signal from an external source. A microcontroller is configured to build a map of the relations between resonant frequencies, permittivities and glucose levels.

Optionally, the device further comprises an LC circuit that includes plates that have fringe flex components projecting from ends of the plates into the blood pool to be sensitivity to permittivity changes in the blood pool. The LC resonant circuit comprises curved plates arranged to face one another with ends of the plates adjacent one another. Optionally, further comprises a microcontroller configured to build a model of a relation between resonant frequencies, and permittivities.

Optionally, the device may comprise a microcontroller configured to collect measurements indicative of the resonant frequency of the LC resonant circuit and calculate data indicative of the resonant frequency. The microcontroller may be further configured to repeat the collecting and calculating operation during at lease first and second test intervals and to determine whether the glucose levels changes between the first and second test intervals.

In accordance with an embodiment herein, a method is provided that comprises implanting a blood glucose sensing device within a cardiovascular pathway of a patient, the sensing device includes an inductor-capacitor (LC) circuit that has a blood glucose sensitive resonant frequency that varies in response to changes in blood glucose levels of the blood. The method generates an excitation signal to excite the LC resonant circuit. The method collects measurements indicative of the resonant frequency of the LC resonant circuit and calculates data indicative of a glucose level of the blood based on the measurements indicative of the resonant frequency.

Optionally, the generating, collecting and calculating operations are repeated during at least first and second test intervals, the method further comprising determining whether the glucose level changes between the first and second test intervals. Optionally, the method calculates a permittivity of the blood based on the measurements and identifying a change in the glucose level based on a change in the permittivity of the blood over time. The calculating operation includes comparing the change in the permittivity to a threshold, and wherein the identifying operation identifies that the glucose level has changed when the change in permittivity exceeds the threshold. Optionally, the method determines the resonant frequency based on the measurements and determining a permittivity of the blood proximate to the LC resonant circuit based on the resonant frequency.

Optionally, the generating operation includes generating the excitation signal from an external source outside of the patient. The generating operation includes generating the excitation signal from an implantable device within the patient. Optionally, the method may comprise an implantable device which may include the blood glucose sensing device.

DETAILED DESCRIPTION

Figure 1A:
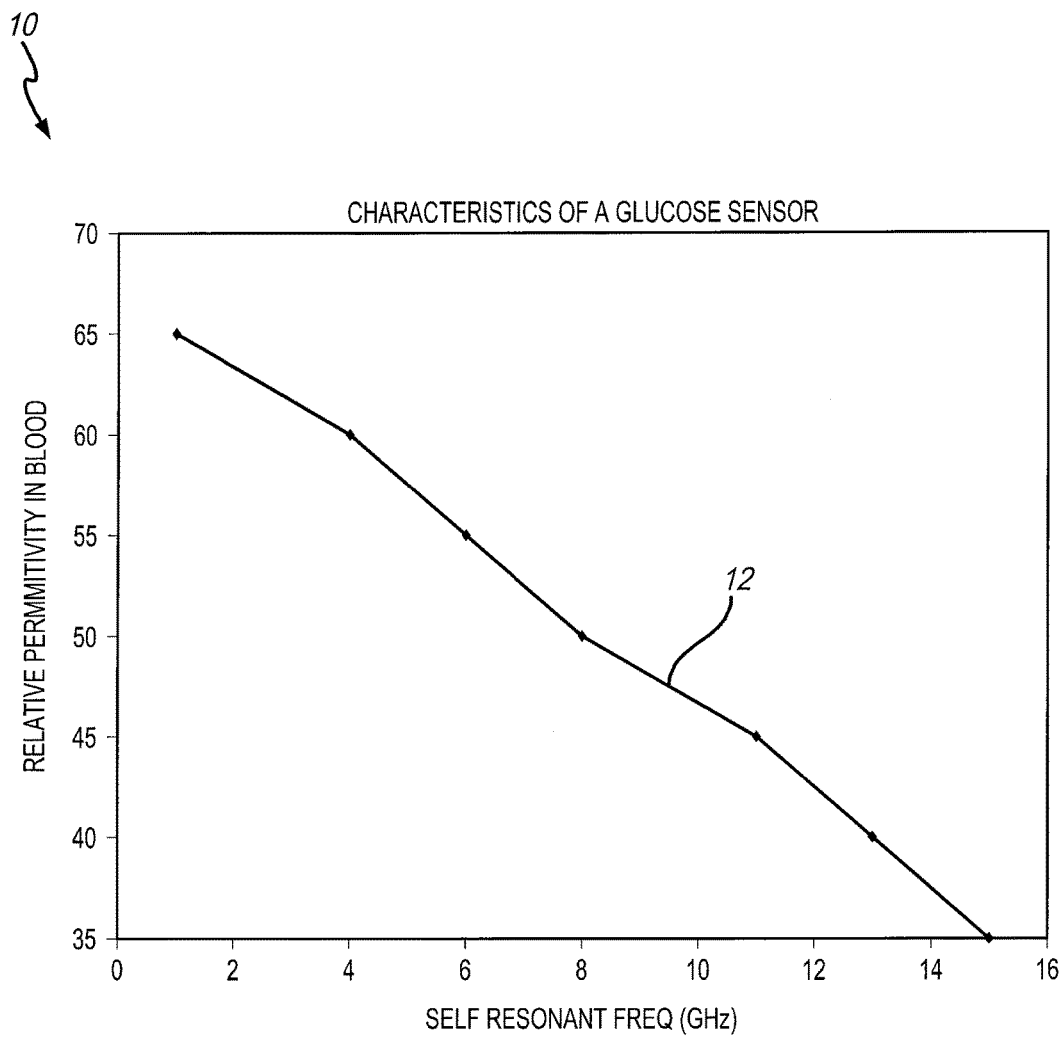
FIG. 1A illustrates a graphical model of a relation between relative permittivity and self-resonant frequency of an LC resonant circuit utilized in accordance with embodiments herein.

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

In accordance with embodiments herein, methods and devices utilize the interaction between blood cellular membrane potential and electromagnetic principles to detect changes in glucose levels. Blood exhibits a certain electrolyte balance that is based in part on cellular membrane potential. When glucose levels change, the transmembrane electrolyte balance is disrupted due to a glucose-induced fluid shift. The fluid shift causes changes in the cell membrane potential. Variations of the metabolically active enantiomer D-glucose affect the permittivity and conductivity of the cellular membranes. Hence, glucose-induced water and ion transport across the cellular membrane leads to changes in the electrical properties of the cellular and consequently extracellular compartments.

In accordance with embodiments herein, variations in electromagnetic waves are used to measure blood glucose levels. The mechanism of using electromagnetic waves for glucose concentration is based on the changes of the dielectric properties of blood. By way of example, a blood glucose sensing device may be incorporated into various structures that are located within the cardiovascular system. For example, cardiac rhythm management (CRM) devices (e.g., pacers, implantable cardioverter defibrillators, cardiac rhythm management devices or leadless pacers) are positioned within the blood flow system. The glucose device may be implemented within a CMEMS circuit which represent a micro-electromechanical system (MEMS) merged with a complementary metal oxide semiconductor (CMOS) circuit. The glucose sensing device may be implanted within various chambers of the heart (e.g. RV, RA and LV or RA) which enable the elimination of several variables associated with external devices. Measuring glucose concentration by a sensor on a lead or CMEMs or leadless pacer (LP) provides continuous, highly accurate glucose monitoring.

Embodiments herein provide methods and devices that utilize electromagnetic technology based glucose sensors on a pacing lead, a CRM device, a CMEMS sensor or LP that would detect glucose concentration in the blood surrounding the lead or the sensor. Embodiments herein provide non-invasive glucose monitoring for better management of heart failure co-morbidities therefore reducing hospitalization and health care costs.

FIG. 1A illustrates a graphical model of a map between permittivity and self-resonant frequency of an LC resonant circuit utilized in accordance with embodiments herein. The relation between permittivity and resonant frequency may be determined through modeling, in vitro testing or otherwise. The model 10 (also referred to as a P-SPF model) assumes that the LC resonant circuit is surrounded with or located proximate to a fluid (e.g., blood) that exhibits shifting permittivity due to glucose concentration. The model 10 plots relative permittivity along the vertical axis (normalized to no unit) and self-resonant frequency (SRF) along the horizontal axis (in GHz). The model 10 includes an example permittivity-SRF graph 12 that shows permittivity of the surrounding fluid in the presence of an LC resonant circuits.

The graph 12 corresponds to a changing glucose level and illustrates the relation between various resonant frequencies of an LC resonant circuit and a corresponding amount of permittivity exhibited by surrounding blood. By way of example, the permittivity-SRF graph 12 illustrates that, for a given LC circuit, when the permittivity within the blood is relatively high (e.g. 65) the LC resonant circuit exhibits a low SRF (e.g. near approximately 1 GHz). When the glucose concentration changes, this reduces blood permittivity, and thus the LC resonant circuit exhibits a higher SRF (e.g., the SRF is approximately 8 GHz, when the blood exhibits a permittivity of approximately 50). As additional examples, the graph 12 shows that a blood pool having a corresponding glucose concentration and a permittivity of 55 will cause the LC resonant circuit to exhibit an SRF of about 6 GHz. When the permittivity is 45, the LC resonant circuit will exhibit an SRF of approximately 10 GHz. The graph 12 may vary based on the particular LC resonant circuit. The graph 12 represents one example of how the SRF varies for a particular LC resonant circuit relative to the amount of glucose in the blood pool.

The model 10 may be determined for individual patients, for each LC resonant circuit, for types of LC resonant circuits and the like. As explained herein, once the model 10 is determined, changes in the glucose concentration may be determined by monitoring changes in SRF, such as relative to baseline SRF characteristics. Embodiments herein maintain a permittivity glucose relation between various permittivity levels and glucose levels and P-SPF model 10. The permittivity-glucose (PG) relation and P=SPF model 10 may be predetermined through laboratory work, while calibration can be done periodically though operation or at other times. One or more PG relations and P-SPF models 10 may be stored in a data store in an LIMD, sensor device, external device, network system, locally or remotely. The PG relation and P-SRF model 10 are used to determine glucose levels.

Figure 1B:
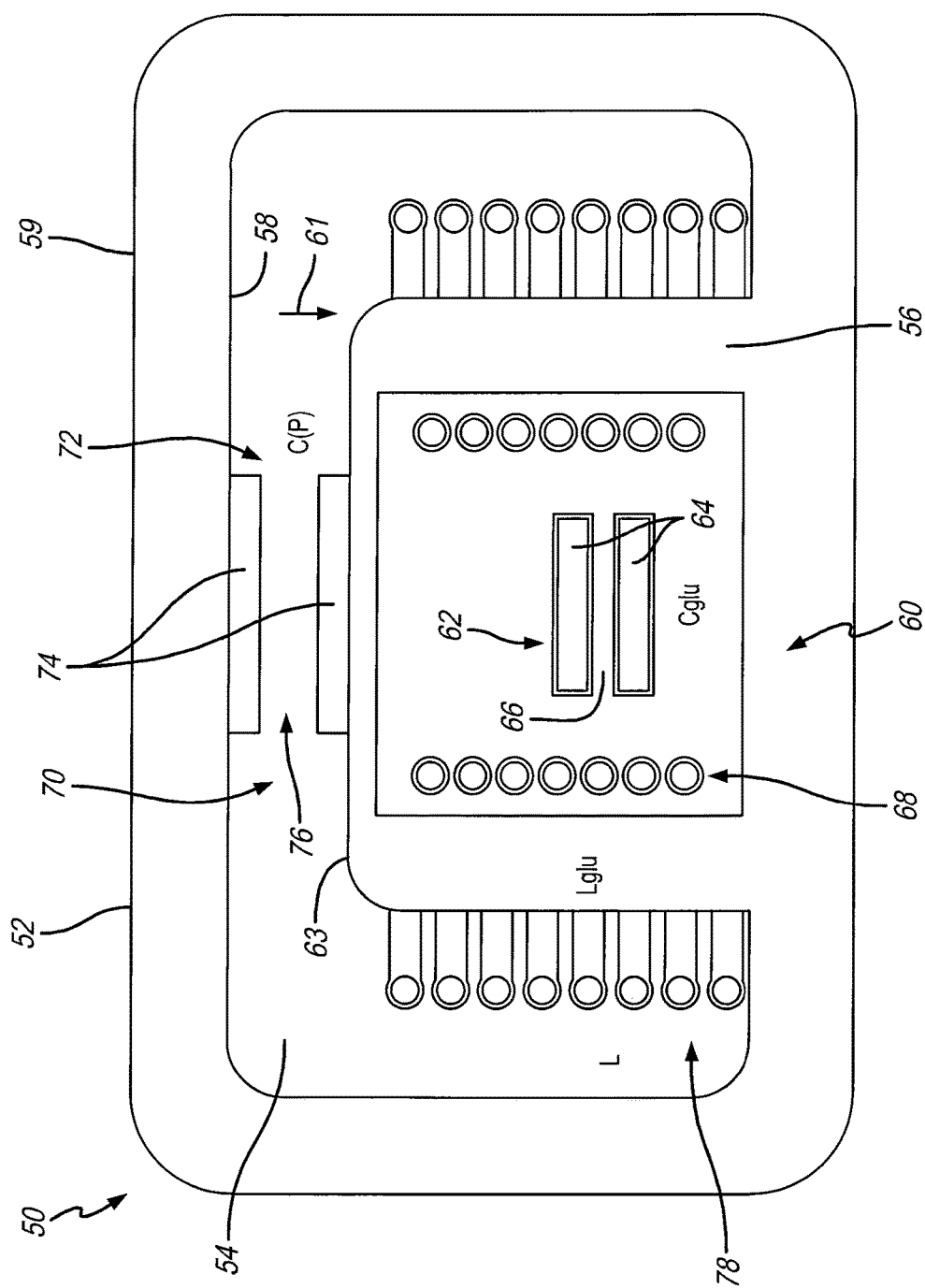
FIG. 1B illustrates a side sectional view of a sensing device formed in accordance with an embodiment herein.

FIG. 1B illustrates a side sectional view of a sensing device 50 formed in accordance with an embodiment herein. The device 50 includes a housing 52 that hermetically encloses an interior space 54. The interior space 54 includes a base member 56 that extends into the interior space 54 from one wall toward an opposing wall 58. The base member 56 encloses a first LC resonant circuit 60 and supports a second LC resonant circuit 70 upon an exterior of the base member 56. The LC resonant circuit 60 is located within the interior space 54 of the housing 52.

The first LC resonant circuit 60 includes a capacitive circuit 62 comprising one or more parallel plates 64 that are separated by a dielectric material 66. The parallel plates 64 are held in a fixed position and relation to one another. The first LC resonant circuit 60 further includes an inductive circuit 68 that comprises a coil conductor wound within the base member 56 about the capacitive circuit 62. Other structures may be employed for the capacitive circuit 62 and inductive circuit 68. The capacitive and inductive circuits 62 and 68 may be electrically coupled to one another in parallel or in series. The capacitive and inductive circuits 62 and 68 have capacitance and inductance values that define a blood glucose sensitive resonant frequency such that a resonant frequency of the LC resonant circuit 60 varies in response to changes in blood glucose level in the cardiovascular pathway surrounding the housing 52. More specifically, the resonant frequency changes in response to changes in permittivity of the blood (caused by changes in the blood glucose level). The resonant frequency is sufficiently high (along the patterns in FIG. 1B) that changes in permittivity are distinguishable from one another based on changes in the resonant frequency.

Optionally, the plates 64 of the capacitive circuit 62 may be oriented longitudinal bottom and/or perpendicular to the top exterior surfaces of the housing 52 or in other orientations to enhance the sensitivity of fringe flex fields to blood permittivity.

The second LC resonant circuit 70 includes a capacitive circuit 72 that comprises one or more parallel plates 74 that are separated by an open area 76. The parallel plates 74 may be moved closer to or further from one another based upon a pressure difference experienced between the interior space 54 and exterior of the housing 52. For example, as the pressure against the exterior surface 59 increases, the wall 58 moves in the direction of arrow 61 towards the upper surface 63 of the base member 56. When the wall 58 moves toward the base member 56, the spacing between the plates 74 reduces thereby changing the capacitance value of the capacitive circuit 72. Similarly, as the pressure against the exterior surface 59 decreases, the wall 58 moves in a direction opposite to arrow 61 away from the upper surface 63 of the base member 56, thereby changing the capacitance value of the capacitive circuit 72 in an opposite direction.

The second LC resonant circuit 70 further includes an inductive circuit 78 that comprises a coil conductor wound about an exterior of the base member 56. Other structures may be employed for the capacitive circuit 72 and inductive circuit 78. The capacitive and inductive circuits 72 and 78 may be electrically coupled to one another in parallel or in series. The capacitive and inductive circuits 72 and 78 have capacitive and inductive values that define a pressure sensitive device such that the resonant frequency of the second LC resonant circuit 70 varies in response to changes in pressure in the cardiovascular pathway surrounding the device 50. For example, the pressure sensitive LC resonant circuit 70 maybe included similar to the pressure sensitive LC resonant circuits described in Patent Application Publication US 2014/010627, the complete subject matter of which is expressly incorporated herein by reference in its entirety.

Figure 1C:
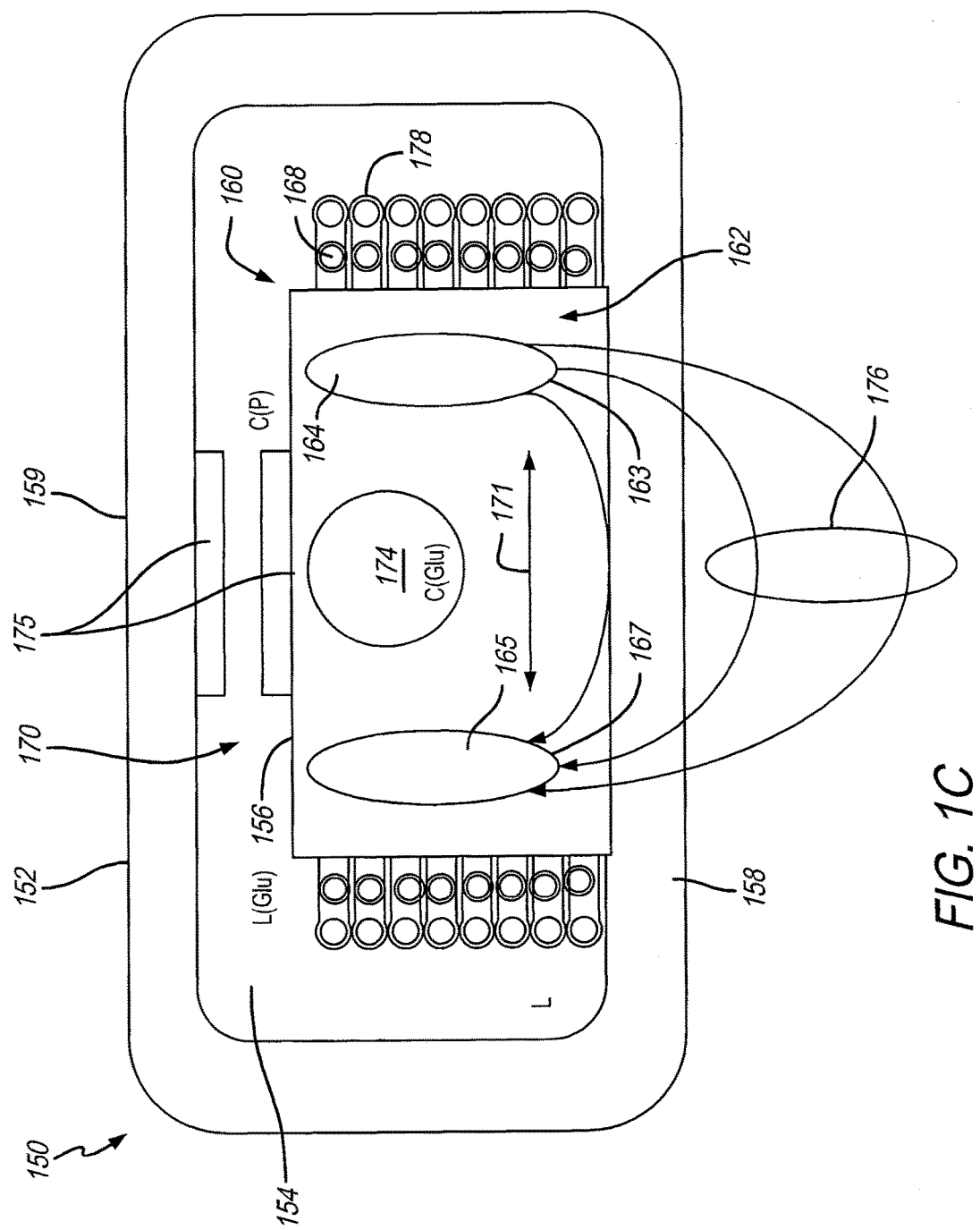
FIG. 1C illustrates a side sectional view of a sensing device formed in accordance with an alternative embodiment.

FIG. 1C illustrates a side sectional view of a blood glucose sensing device 150 formed in accordance with an alternative embodiment. The device 150 includes a housing 152 that hermetically seals an interior space 154. The housing 152 includes opposed longitudinal walls 158 and 159. A base member 156 is located along an interior surface of wall 158. The base member 156 encloses a first capacitive circuit 162 that is formed from capacitor plates 164 and 165. The capacitor plates 164 and 165 are separated by a dielectric material defined by the base member 156. The plates 164, 165 are held in a fixed position and relation to one another. The capacitor plates 164 and 165 include lateral edges 163 and 167 that are directed toward, and located proximate to, the wall 158 of the device 150. A spacing between the plates 164, 165 extends in a direction (generally denoted at 171) that is parallel to, and located relatively proximate to, the wall 158.

During operation, an electric field is generated between the plates 164 and 165. The electric field is comprised of various field flux components. For example, the electric field includes a main flux component 174 that is located within the dielectric material of the base member 156 in the space 171 and is positioned immediately between facing surfaces of the plates 164 and 165. The electric field also includes fringe flux components 176 that extend between the lateral edges 163 and 167 of the plates 164 and 165. The fringe flex components extend laterally in opposite directions from the plates 164, 165; however, for simplicity only the fringe flex components 176 are illustrated. The fringe flux components 176 project along field lines that extend through the walls 158 and 159 into the surrounding blood. As the glucose concentration in the blood various, the permittivity similarly various. The fringe flux component 176 passes through the surrounding blood and thus is exposed to the corresponding blood permittivity.

The first LC resonant circuit 160 further includes an inductive circuit 168 that comprises a coil conductor wound about a perimeter of the base member 156 and about the capacitive circuit 162. Other structures may be employed for the capacitive circuit 162 and inductive circuit 168. The capacitive and inductive circuits 162 and 168 may be electrically coupled to one another in parallel or in series. The capacitive and inductive circuits 162 and 168 have capacitance and inductance values that define a blood glucose sensitive resonant frequency such that a resonant frequency of the LC resonant circuit 160 varies in response to changes in blood glucose level in the cardiovascular pathway surrounding the housing 152.

Optionally, additional physical configurations may be provided to locate larger portions of the fringe flux component 176 within the blood. For example, the plates 164, 165 may be positioned such that lateral edges on opposite sides of each plate 164 and 165 are located immediately adjacent the exterior surfaces of the walls 158, 159 of the housing 152. By locating the lateral edges on both sides of the plates 164 and 165 immediately adjacent to the exterior of the housing 152, a substantial portion of the fringe flux components 176 on both sides of the capacitive circuit 162 are largely exposed to blood.

Additionally or alternatively, the housing 152 may be constructed such that a portion of the main flux component 174 passes through blood. For example, a hollow passage (similar to a doughnut hole) may be created through the core of the base member 156 and housing 152 such that blood may pass through the open core without being exposed to the interior 154. As another example, a notch may be formed in a side of the wall 158 that extends into the portion of the base member 156 located between the plates 164 and 165. The notch may create a cavity (e.g. a U-shaped cavity, a C-shaped cavity, etc.) that is exterior to the housing 152, but located between the plates 164 and 165.

Optionally, the device 150 may include a second LC resonant circuit 170 having a capacitive circuit 72 comprises one or more parallel plates 175 that are separated by an open area. The parallel plates 175 may be moved closer to or further from one another based upon a pressure difference experienced between the interior space 154 and exterior of the housing 152. For example, as the pressure against the exterior surface increases, the wall 159 moves towards the upper surface of the base member 156. The second LC resonant circuit 170 further includes an inductive circuit 178 that comprises a coil conductor wound about an exterior of the base member 156. The inductive circuits 158 and 178 are wound concentrically with one another as one example.

Figure 1D:
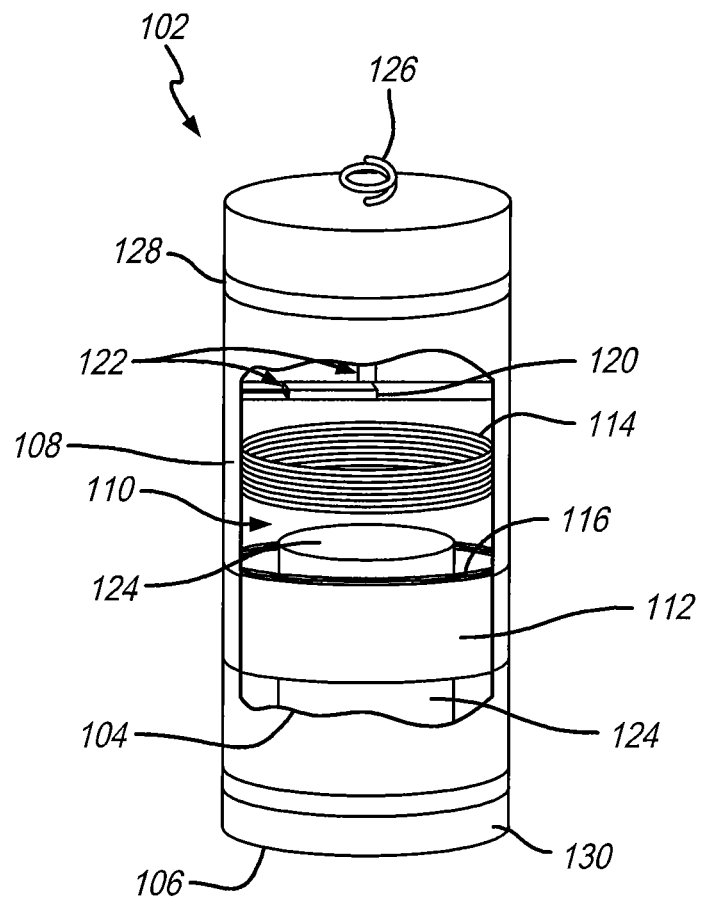
FIG. 1D illustrates an embodiment of a leadless glucose sensing device formed in accordance with an alternative embodiment.

FIG. 1D illustrates, in a simplified sectional side view, an embodiment of a leadless glucose sensing device 102. For purposes of illustration, the device 102 is depicted with a hypothetical opening 104 to show several interior components of the device 102. The device 102 includes a housing 106 comprising an external surface 108 and defining an interior space 110. The sensing device 102 is described in connection with a first LC resonant circuit sensitive to blood glucose. Optionally, the sensing device 102 may also include a second LC resonant circuit sensitive to changes in blood pressure similar to the pressure sensitive LC resonant circuits in the '627 application.

The device 102 comprises an LC resonant circuit glucose sensor including a capacitive circuit 112 and an inductive circuit 114. In the example of FIG. 1D, the capacitive circuit 112 comprises one or more concentric plates 116 separated by dielectric material and the inductive circuit 114 comprises a coil inductor. The device 102 includes circuitry to detect changes in a resonant frequency of the LC resonant circuit (e.g., circuit 62 and/or circuit 70 in FIG. 1B) and based thereon, generate data indicative of glucose levels. For example, an integrated circuit 120 (having one or more processors), one or more associated electrical conductors 122, and a battery circuit 124 (comprising a battery) may be coupled to the LC-resonant circuit(s) for detecting the operating frequency of the LC resonant circuit(s), identifying permittivity calculating glucose levels, identifying pressure levels, and/or for exciting the LC resonant circuit(s). The integrated circuit 120, the electrical conductors 122, and the battery circuit 124 are located within the interior space 110 of the housing 106.

In a typical implementation, one terminal of the inductive circuit 114 is coupled via a conductor to a plate of the capacitive circuit 112, while another terminal of the inductive circuit 114 is coupled via another conductor to another plate of the capacitive circuit 112. Thus, the inductive circuit 114 and the capacitive circuit 112 are coupled in parallel, thereby forming a resonant circuit that is capable of being excited by an externally applied electromagnetic field or an internally applied signal. Alternatively, the circuits 112 and 114 may be coupled in series.

Optionally, the device 102 may include components for sensing cardiac signals and/or stimulating (e.g., pacing) cardiac tissue. For example, the device may operate in one or more of the following modes: VDD, DDD, VVIR, CRT, or some other suitable mode. These components may include, for example, an electrode 126 (e.g., a helical electrode), an electrode 128 (e.g., a ring electrode), one or more additional electrodes (represented by electrode 130), and other circuitry. This other circuitry may include, for example, corresponding functionality of the integrated circuit 120, one or more of the electrical conductors 122, and the battery circuit 124.

Figure 1E:
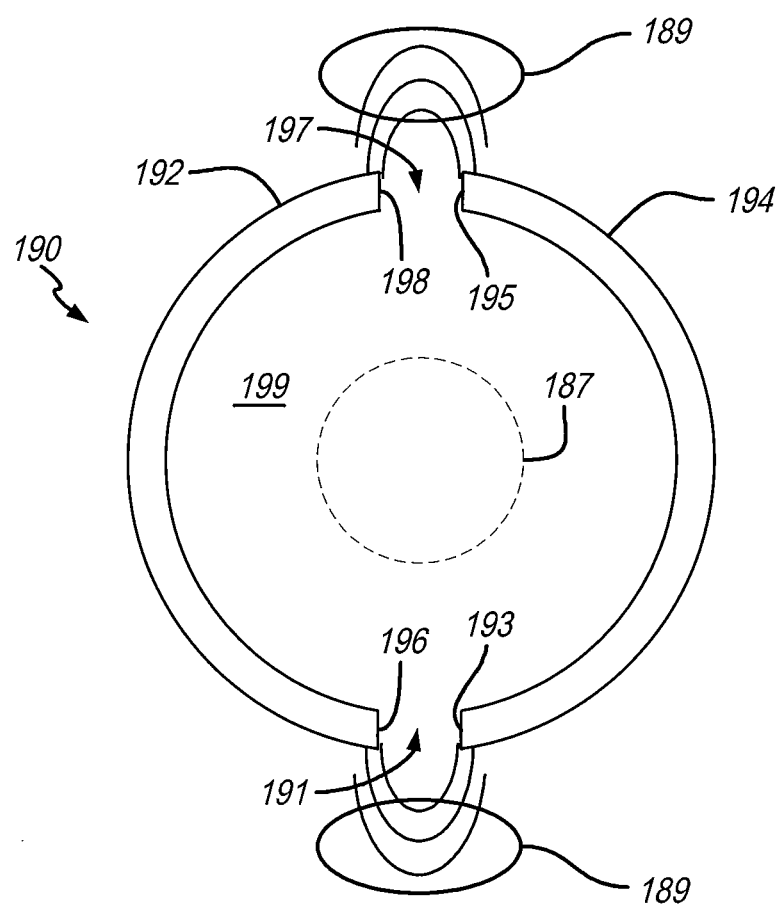
FIG. 1E illustrates a capacitive circuit formed in accordance with an alternative embodiment.

FIG. 1E illustrates a configuration for a capacitive circuit 190 formed in accordance with an alternative embodiment. The capacitive circuit 190 includes curved capacitor plates 192 and 194. The capacitor plate 192 includes opposed lateral ends 196 and 198. The capacitor plate 194 includes opposed lateral ends 195 and 193. The capacitor plates 192 and 194 are curved or semicircular in shape and positioned in a non-concentric configuration such that the ends 196 and 193 are located proximate to one another and face one another, while the ends 198 and 195 are similarly located proximate to and facing one another. The curved capacitor plates 192 and 194 collectively define an overall circular shape with each plate 192 and 194 forming a curved open portion of the circular shape. The plates 192 and 194 are spaced apart from one another, such that circumferential gaps 197 and 191 are located between the ends 193, 195, 196 and 198. The gaps 191, 197, as well as a core region 199 may be filled with a dielectric material to maintain the plates 192 and 194 in a fixed relation to one another, but spaced apart from one another.

During operation, an electric field is formed between the plates 192 and 194, where the electric field includes a main flux component in the core region 199 and fringe flux components in the regions 189 that flare radially outward from the gaps 191, 197. At least the regions 189 are located within the blood pool surrounding the device such that the fringe flux components are exposed to changes in the permittivity of the blood.

Optionally, a portion of the core region 199 may be rendered hollow such that blood may pass through the region 199 (such as denoted by the circular dashed line 187). By permitting blood to pass through the region 199 through which the main flux components pass, the capacitive circuit 190 may become more sensitive to permittivity changes. Optionally, more than two capacitor plates may be utilized. For example, more than a single capacitor may be provided within the capacitive circuit 190 (or any of the lead or device described herein).

The capacitive circuit 190 may be provided within the device 102 in addition to, or in place of, the capacitive circuit 112. The capacitive circuit 190 is coupled to the corresponding inductive circuit (e.g. 114 in FIG. 1D).

Figure 2A:
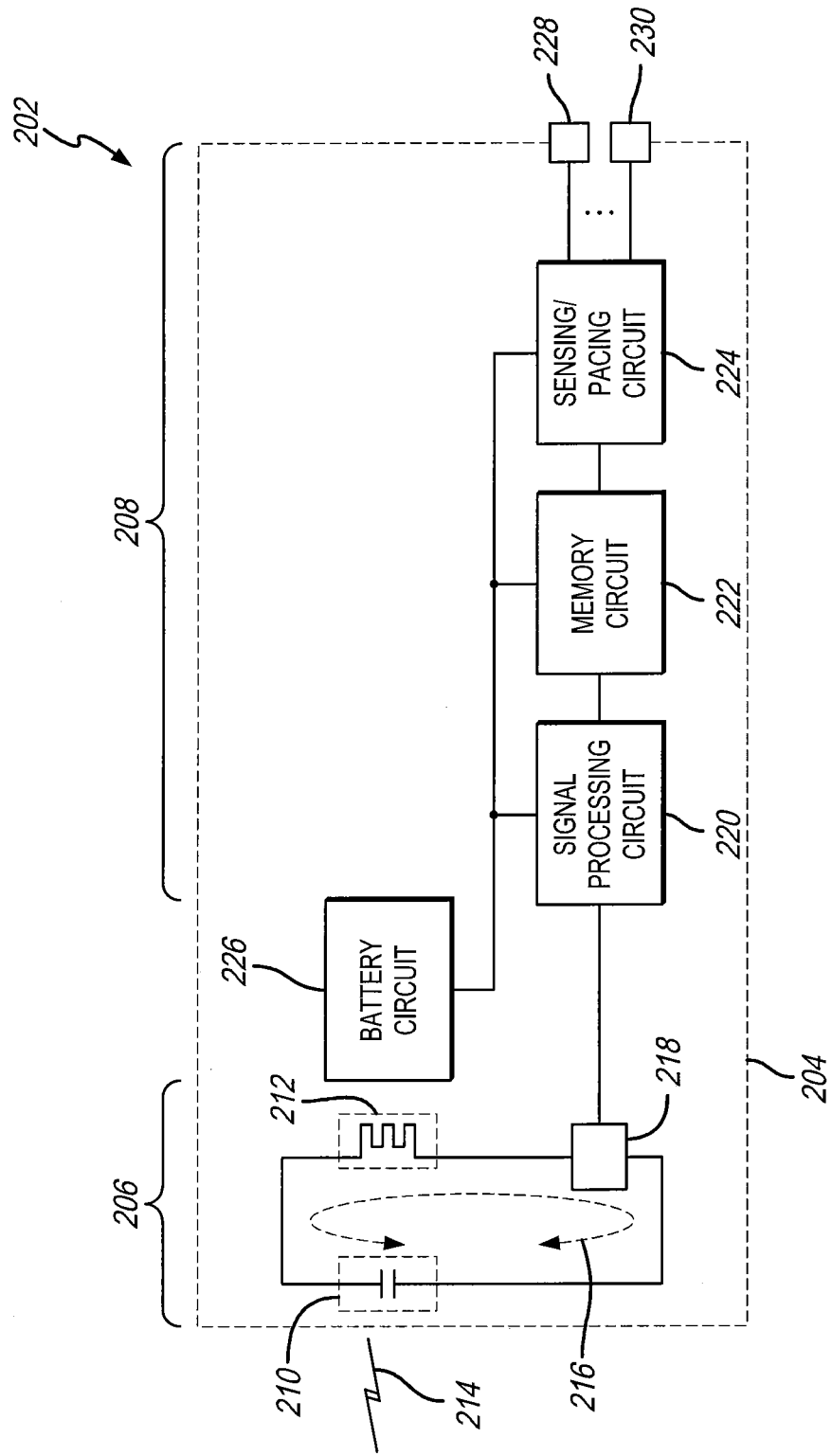
FIG. 2A illustrates a simplified block diagram of an embodiment of a leadless glucose sensing device that comprises a passive LC resonant circuit glucose sensor.

FIG. 2A is a simplified block diagram of an embodiment of a leadless glucose sensing device 202 that comprises a passive LC resonant circuit glucose sensor. The housing is represented by a dashed line 204. The LC resonant circuit 206 is located at the left-most section of the device 202, while the circuit 208 to the right of the LC resonant circuit 206 performs certain glucose level sensing-related operations as well as cardiac sensing and/or pacing operations. For purposes of illustration, the circuit 208 is depicted as including a signal processing circuit 220 (including one or more processors), a memory circuit 222, a sensing/pacing circuit 224, a battery circuit 226, and two electrodes 228 and 220. It should be appreciated that different combinations of these components may be employed in other embodiments constructed in accordance with the teachings herein.

The LC resonant circuit 206 comprises a capacitive circuit 210 and an inductive circuit 212. The inductance and capacitance values of these components are selected to cause the LC resonant circuit 206 to resonate at a select reference frequency when in the presence of blood having a corresponding reference or select glucose level. In this case, the LC resonant circuit 206 is excited (e.g., induced with a signal that causes the LC resonant circuit 206 to resonate) by an externally generated radiofrequency (RF) signal 214. As one example, the RF signal 214 maybe generated by an external antenna that may be help against the patient or provided within another common structure used by the patient. For example, the antenna may be provided under a bed, within a pillow, within a chair back, automobile seat back, handheld and the like. The antenna is connected to an external device such as a bedside monitor, a portable computer, smart phone, smart watch and the like. Upon excitation, an oscillating signal 216 (represented, for convenience, by a dashed line) at the resonant frequency is established in the LC resonant circuit 206.

The capacitance and inductance values for the capacitive circuit 210 and inductive circuit 212 are set to define a blood glucose sensitive resonant frequency such that a resonant frequency of the LC resonant circuit 206 varies in response to changes in blood glucose levels within the blood in the cardiovascular pathway surrounding the housing. A change in the blood glucose level will result in a change in a permittivity characteristic (and/or other electrical characteristic) of the blood. The change in permittivity, in turn, causes a change in the resonant frequency of the LC resonant circuit 206. Thus, a change in glucose level will correspond to a change in the frequency of the oscillating signal 216.

The circuit 218 collects measurements indicative of the resonant frequency. For example, the oscillating signal 216 is detected by the circuit 218 (e.g., a high impedance sense amplifier, a low impedance current sensing circuit, or some other suitable circuit) and provided to the signal processing circuit 220. The signal processing circuit 220 processes the measurements of the received signal to determine at least one frequency of the signal. The signal processing circuit 220 utilizes the frequency to calculate data representative of the glucose level of the blood surrounding the device 202.

The signal processing circuit 220 may then store this data in the memory circuit 222 for subsequent use. For example, as discussed below, the device 202 may periodically collect data over a period of time, and send the stored data to an external device at some later point in time. As another example, one or more operating parameters (e.g., pacing parameters) of the device 202 may be adjusted based on the glucose data. To facilitate receiving the oscillating signal 216, the signal processing circuit 220 and/or the circuit 218 may comprise one or more of: a sensing circuit, an amplifier, a filter, a switching circuit, or other suitable circuits. These circuits may perform one or more of: detecting, filtering, or amplifying the oscillating signal 216.

As represented by corresponding lines in FIG. 2A, the battery circuit 226 is electrically coupled to one or more of the circuits 218-224 and any other circuits (not shown) that require power from the battery circuit 226. It should be appreciated that the battery circuit 226 may be implemented using any suitable implantable power source.

The signal processing circuit 220 is also electrically coupled to each electrode 228 and 230 (e.g., via the circuit 224) for sensing cardiac activity and/or stimulating cardiac tissue. Thus, in some cases, the electrodes 228 and 230 are used for stimulating cardiac tissue. In some cases, one or more of the electrodes 228 and 230 may be used for sensing cardiac activity (e.g., for near-field sensing and/or far-field sensing). For example, the electrodes 228 and 230 may correspond to the electrodes 126 and 128 of FIG. 1B (or some other combination of the electrodes of FIG. 1B).

The sensing/pacing circuit 224 is electrically coupled to the electrodes 228 and 230 to receive electrical signals indicative of cardiac activity and/or to output cardiac stimulation signals (e.g., pacing pulses). To facilitate interfacing with these components, the sensing/pacing circuit 224 may comprise one or more of: a sensing circuit, an amplifier, a filter, a signal generator, a signal driver, a switching circuit, or other suitable circuits. Thus, the sensing/pacing circuit 224 may filter, amplify, and detect signals received from the electrodes 228 and 230. In addition, the sensing/pacing circuit 224 may generate, filter, and amplify signals sent to the electrodes 228 and 230.

The signal processing circuit 220 may process cardiac signals received via the sensing/pacing circuit 224 to identify cardiac events. For example, a microprocessor of the signal processing circuit 220 may be configured to acquire intra-cardiac electrogram data (and/or other cardiac related signal data) and identify P waves, R waves, T waves and other cardiac events of interest. Based on analysis of these cardiac events, the processing circuit may selectively generate stimulation signals (e.g., pacing pulses) to be delivered to cardiac tissue via one or more electrodes. The signal processing circuit 220 also may control stimulation operations by controlling the signals generated by the sensing/pacing circuit 224. For example, a microprocessor of the signal processing circuit 220 may be configured to trigger the generation of pacing signals, specify pacing signal characteristics (e.g., energy level and duration), and inhibit pacing signals.

It should be appreciated that the signal processing circuit 220 may take various forms in different embodiments. For example, in some implementations, a single circuit (e.g., a microprocessor) may be employed to handle processing for both glucose sensing and cardiac operations. In other implementations, however, different circuits may be employed to provide the processing for these different operations.

Furthermore, in some embodiments, the resonant frequency of the LC-resonant circuit 206 may be determined by an external device. In such a case, the leadless glucose sensing device 202 need not employ the circuit 218 or the capability of generating data representative of cardiac glucose. Rather, based on the resonant frequency determination made by the external device, the external device will determine the blood glucose level.

Embodiments herein calculate a self-resonant frequency of the LC resonant circuits and calculate corresponding blood permittivity, glucose levels and pressure in various manners. As one example, a template may be constructed that maps various SRF to permittivity levels, where the map or template includes multiple graphs plotting functional relations between permittivity and SRF, each graph associated with a corresponding glucose level. Next, methods are described in connection with FIGS. 2B and 2C for building the maps and utilizing the maps during glucose testing.

Figure 2B:
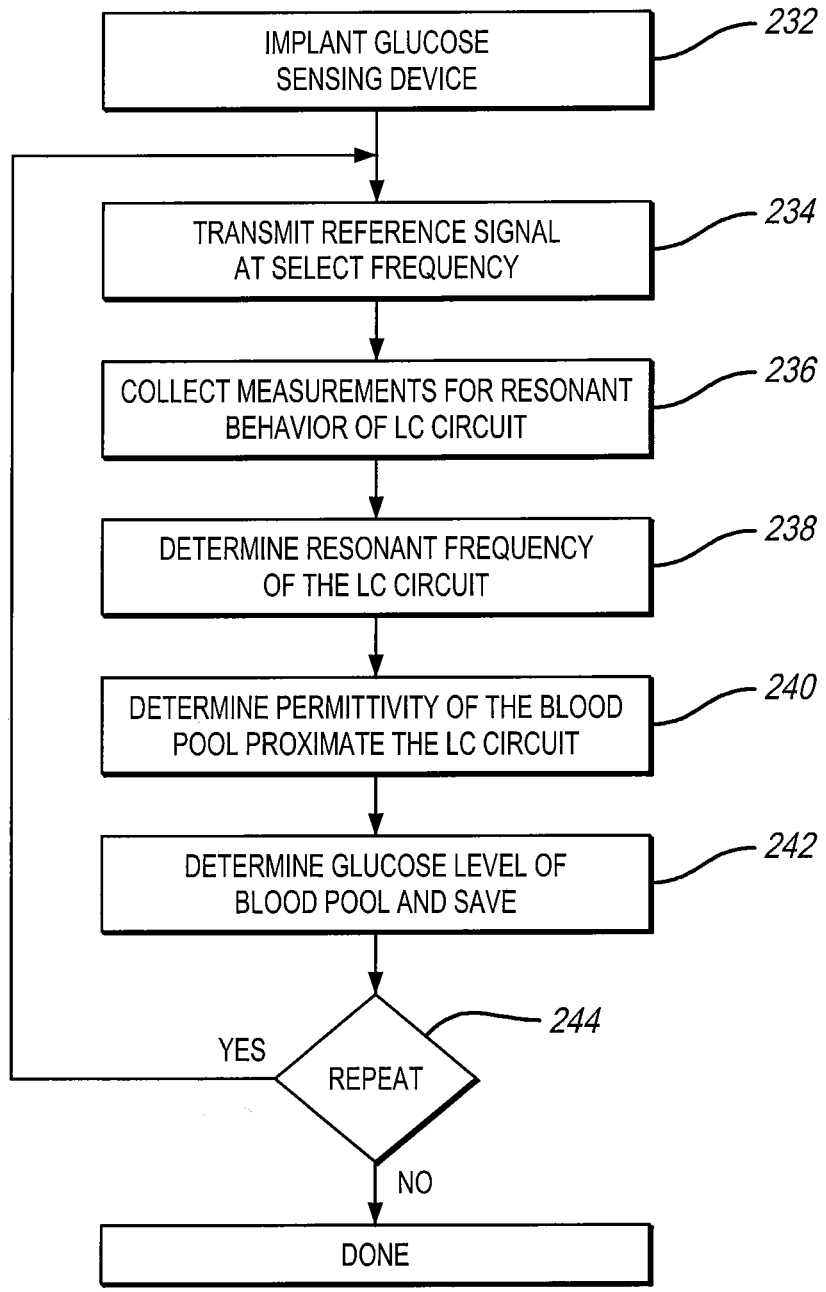
FIG. 2B illustrates a method for building a map of permittivity to SRF relations for different glucose concentrations in accordance with embodiments herein.

FIG. 2B illustrates a method for building a map of the permittivity to SRF relation or pattern for a given LC resonant circuit and a blood pool that experienced different select levels of glucose concentration. The method may be performed before implant at the time a device is manufactured and/or after device implant. The map may be based on models, lab work or otherwise, where each LC circuit need not be test. At 232, a glucose sensing (GS) device is implanted at a location proximate to a blood pool to be monitored. For example, the GS device may be implanted proximate to a chamber of the hear, such as in the RV, LV, RA, LA, and/or in the great vessels of the heart that enter and leave the heart (e.g., the superior and inferior vena cava, the pulmonary artery, the pulmonary vein, and the aorta). The GS device may be located proximate to other portions of the vascular system provided that a sufficient amount of blood surrounds or is located at a proximity to the LC resonant circuit such that the permittivity of the blood pool affects the resonant frequency of the LC resonant circuit. The amount of blood and/or the available distance between the blood pool and the LC resonant circuit will vary depending on a construction of the LC resonant circuit, a sensitivity of the LC resonant circuit, the type of excitation source utilized and other design factors.

At 234, the system transmits a reference excitation signal. The excitation signal may be generated by an external RF transmitter source, such as an antenna located near the patient. Optionally, the excitation signal may be generated by an implanted transmitter source, such as within an IMD, a leadless pacemaker or other implanted device. The reference excitation signal may be generated by the same implanted device (e.g., IMD or LP) that includes the glucose sensing device. Optionally, the LC resonant circuit may be used to generate the reference excitation signal, such as when the LC resonant circuit is driven by an oscillator. The reference excitation signal may be maintained at a constant amplitude and frequency through a select test period of time. Alternatively, the amplitude and/or frequency of the reference excitation signal may be varied within a select range during individual transmit intervals over the select test period of time.

At 236, the LC resonant circuit is monitored to collect measurements related to one or more characteristics indicative of the resonant behavior of the LC resonant circuit. For example, the measurements may represent impedance, voltage and/or current measurements across input terminals of the LC resonant circuit. When the LC resonant circuit is implemented within an IMD or LP, a processor or microcontroller therein may collect the impedance, voltage and/or current measurements across the LC resonant circuit. Additionally or alternatively, the measurements may be collected by an external device that measures impedance, voltage and/or current measurements across terminals of a separate transmit or receive antenna external to the patient. The measurements may correspond to an amount of reflection experienced as a transmit antenna and/or the amount of reflection experienced at the LC resonant circuit.

The operations at 234 and 236 may be performed once when using an excitation pulse with multiple frequency components or may be repeated in an iterative manner in connection with multiple reference signals transmitted at various select frequencies to obtain a collection of measurements indicative of the resonant behavior of the LC resonant circuit at the select frequencies.

At 238, the method determines the resonant frequency of the LC resonant circuit based on the measurements collected at 236. The resonant frequency is determined from the measurements utilizing various methods. At 238, the method saves the measurements (collected at 236), the resonant frequency (determined at 238) and, optionally, the parameters defining the reference signals (transmitted at 234).

At 240, the method determines the permittivity of the blood pool that is surrounding or located proximate to the LC resonant circuit. The permittivity may be determined based on the resonant frequency determined at 238. Optionally, the permittivity maybe based on known constant properties of the capacitive circuit and inductive circuit within the LC resonant circuit. By way of example only, one method for determining permittivity for a medium surrounding an LC resonant circuit is described in U.S. Pat. No. 6,014,029, the complete subject matter of which is incorporated herein by reference in its entirety. More than one permittivity level may be determined at 240 based upon corresponding different resonant frequencies, measurements and reference signals collected at 234-238. The permittivity value or values determined at 240 are stored for the present measurement session along with the additional information determined at 234-238.

At 242, the method measures the glucose level of the blood pool proximate to the LC resonant circuit utilizing a secondary measurement device. The glucose level may be measures in various manners, such as by measuring the glucose level directly from a blood sample or other test method. For example, the glucose level may be determined through fluid chemical analysis, breath chemical analysis, infrared spectroscopy, optical coherence tomography, thermal spectroscopy, ocular spectroscopy, fluorescence or impedance spectroscopy. Alternatively, conventional ultrasound, electromagnetic or thermal techniques may be utilized to measure the blood glucose level. At 242, the glucose level is saved in connection with the information generated and saved during the operations at 232-240.

At 244, the method determines whether to repeat the process. For example, the operations at 232-242 may be repeated at different times of day, and/or while a patient is experiencing different levels of physical or other types of stress. The operations at 232-244 may be repeated before and after meals, as well as based on other criteria that may affect a patient's blood glucose level. When it is determined to repeat the process, flow returns to 234. Otherwise, the process ends. Optionally, the operations at 232-244 may be repeated at the time of device implant or during checkups, where the patient's blood glucose is temporarily changed while in the hospital or clinic. Optionally, the operations 232-244 may be performed in a test lab when the device is manufactured before implant.

Each time the operations at 234-242 are repeated, the saved information is updated based on a present measurement/data collection session and stored, to create a map defining patterns between SRF, permittivity and glucose levels for the patient. By way of example only, a map may be recorded that includes all or a portion of the data points illustrated in FIG. 1A. For example, after multiple collection sessions, the data may be determined in connection with a particular patient and LC resonant circuit, where the blood exhibits permittivities of 35 to 65 in connection with corresponding different glucose levels and while the LC resonant circuit exhibits a resonant frequencies of 1 to 15 GHz.

Figure 2C:
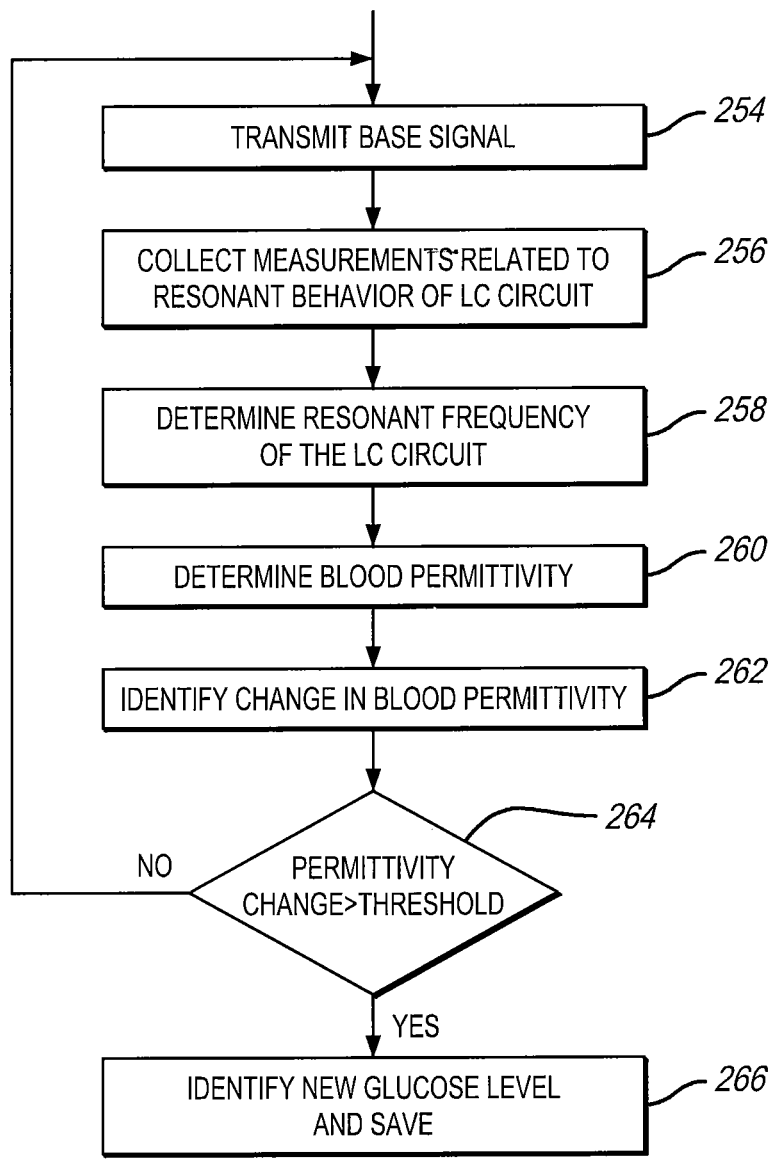
FIG. 2C illustrates a process for monitoring a patient's blood glucose level in accordance with embodiments herein.

FIG. 2C illustrates a process for monitoring a patient's blood glucose level in accordance with embodiments herein. At 254, the system transmits a base excitation signal. The excitation signal may be generated by an external RF transmitter source, such as an antenna located near the patient. Optionally, the base excitation signal may be generated by an implanted transmitter source, such as within an IMD, a leadless pacemaker or other implanted device. Optionally, the base excitation signal may be generated by the same device (e.g., IMD or LP) that includes the glucose sensing device. Optionally, the LC resonant circuit may be used to generate the base excitation signal. The base excitation signal may be maintained at a constant amplitude and frequency for a select test period of time. Alternatively, the amplitude and/or frequency of the base excitation signal may be varied within a select range during an individual transmit interval of the base excitation signal.

At 256, the LC resonant circuit is monitored to collect measurements related to one or more characteristics concerning the resonant behavior of the LC resonant circuit. As noted herein, the measurements may represent impedance, voltage and/or current measurements across the input terminals of the LC resonant circuit. When the LC resonant circuit is implemented within an IMD or LP, a processor or microcontroller therein may collect the impedance, voltage and/or current measurement across the LC resonant circuit. Additionally or alternatively, the measurements may be collected by an external device that measures impedance, voltage and/or current measurements across terminals of a separate transmit or receive antenna.

The operations at 254 and 256 may be performed once with a multi-frequency excitation signal or may be repeated in an iterative manner in connection with multiple base excitation signals transmitted at various select frequencies to obtain a collection of measurements indicative of the resonant behavior of the LC resonant circuit at various frequencies.

At 258, the method determines the resonant frequency of the LC resonant circuit based on the measurements collected at 256. The resonant frequency may be determined from the measurements utilizing various methods.

At 260, the method determines the permittivity of the blood pool that is surrounding or located proximate to the LC resonant circuit. The permittivity may be determined based on the resonant frequency determined at 238, as well as based on the known constant properties of the capacitive circuit and inductive circuit within the LC resonant circuit. By way of example, the measurements may be compared to one or more previously stored P-SPF models and PG relations associated with the current patient or a collection of patients (such as generated in connection with FIG. 2B and illustrated in FIG. 1A). The P=SPF models and PG relations designates permittivity to resonant frequency patterns. The measurements collected at 256 are compared to the P-SPF model to identify a corresponding data point having an associated permittivity of the blood pool and resonant frequency of the LC resonant circuit. The data point corresponds to a glucose level that is derived from the P-SPF model.

At 262, the method compares the current blood permittivity with previously recorded permittivity level or levels to identify an amount and nature of change in the blood permittivity.

At 264, the method determines whether the change in permittivity exceeds a threshold, also referred to as a common glucose level threshold. The threshold corresponds to an amount of change in permittivity that may be experienced without representing a change in blood glucose level. It is recognized that blood permittivity may change for other reasons within certain limits, other than due to glucose level changes. The threshold at 264 is set to differentiate between permittivity changes due to blood glucose and other reasons. When the permittivity change exceeds the threshold, flow moves to 266. Otherwise, flow returns to 254.

At 266, the method identifies a new glucose level associated with the current permittivity value. For example, the new glucose level may be determined based on one or more templates or other information prerecorded in connection with the present patient, and/or in connection with a control group of patients.

Thereafter, the process of FIG. 2C may be repeated or the method may enter an idle state until it becomes desirable to repeat the blood glucose test of FIG. 2C.

Figure 3:
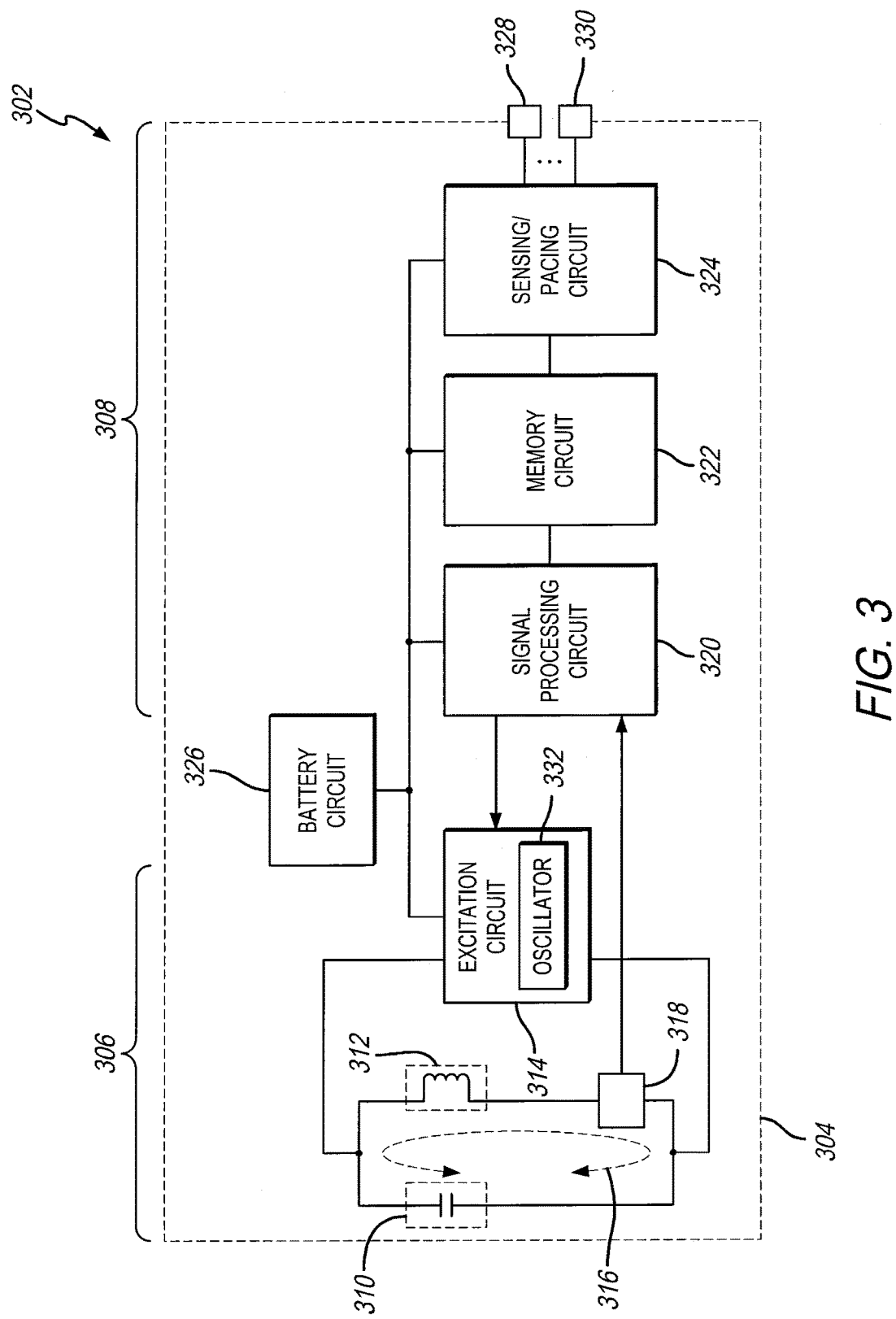
FIG. 3 illustrates a diagram of an embodiment of a leadless glucose sensing device that comprises an active LC resonant circuit glucose sensor.

FIG. 3 is a simplified schematic and block diagram of an embodiment of a leadless glucose sensing device 302 that comprises an active LC resonant circuit glucose sensor. Similar to the device 202 of FIG. 2A, the device 302 comprises a housing 304, an LC resonant circuit 306 and a circuit 308 that performs certain glucose sensing-related operations as well as cardiac sensing and/or pacing operations. The LC resonant circuit 306 comprises a capacitive circuit 310 and an inductive circuit 312. A circuit 318 is configured to sense an oscillating signal 316 of the LC resonant circuit 306. The circuit 308 comprises a signal processing circuit 320 (which includes one or more microprocessors), a memory circuit 322, a sensing/pacing circuit 324, a battery circuit 326, and electrodes 328 and 330. Different combinations of these components may be employed in other embodiments constructed in accordance with the teachings herein.

In this embodiment, the LC resonant circuit 306 is excited by an internal excitation circuit 314 instead of by external excitation signals. The excitation circuit 314 generates a signal (e.g., a single pulse, a set of pulses, or a periodic pulse signal) that serves to excite the LC resonant circuit 306 and, if applicable, maintain oscillations in the LC resonant circuit 306. To this end, the excitation circuit 314 may include an oscillator 332 that generates an excitation signal or some other suitable excitation signal generator circuit.

In some implementations, the signal processing circuit 320 (or some other suitable circuit of the device 302) includes a processor that, among other things, controls the operation of the excitation circuit 314. For example, upon receipt of a suitable command from an external device (e.g., an external monitoring device) at the signal processing circuit 320, the excitation circuit 314 may be controlled to commence excitation of the LC resonant circuit 306. Alternatively, the signal processing circuit 320 may be configured to initiate excitation at certain times (e.g., periodically). Concurrent with either of the above operations, the processor of the signal processing circuit 320 may commence processing of the received oscillating signal 316 and generating data representative of the glucose level in the surrounding blood.

Figure 4:
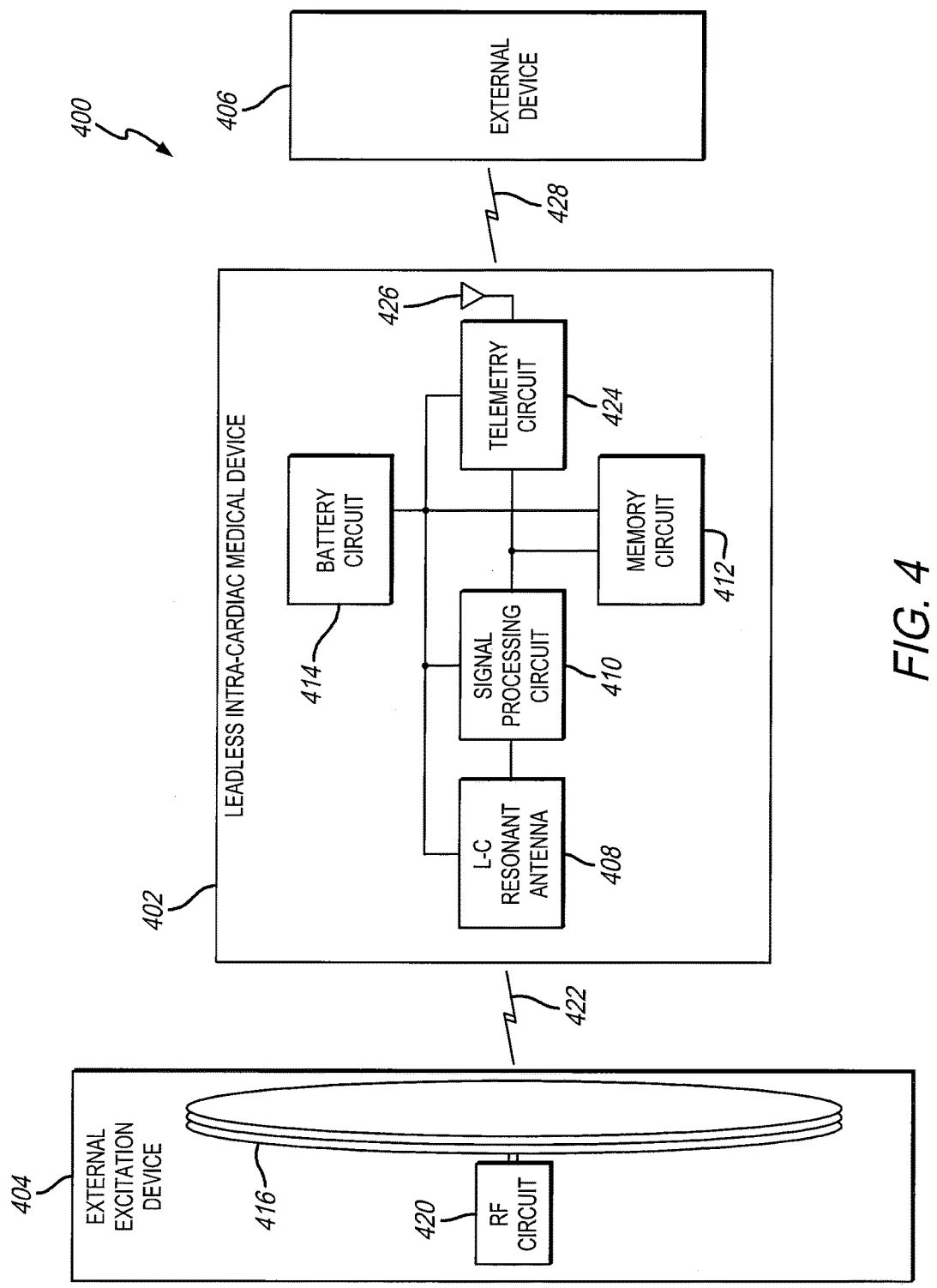
FIG. 4 illustrates an embodiment of a system where an implanted leadless glucose sensing device communicates with an external device and an external device.
Figure 5:
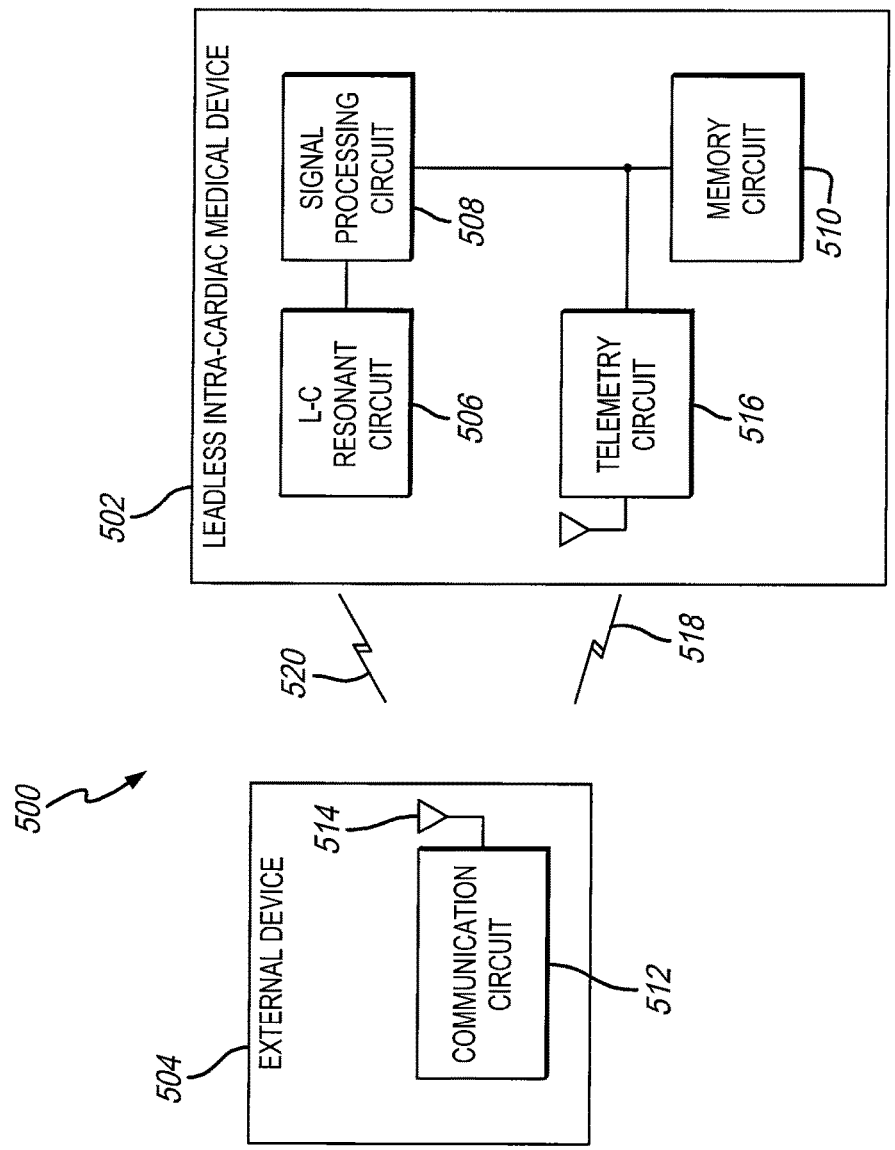
FIG. 5 illustrates an embodiment of a system where an implanted leadless glucose sensing device communicates with an external device.

A leadless glucose sensing device may communicate with external devices in different ways in different embodiments. FIGS. 4 and 5 depict two examples illustrating how a leadless glucose sensing device may communicate with different types of external devices.

FIG. 4 illustrates an embodiment of a system 400 where a leadless glucose sensing device 402 that is implanted in a patient (not shown) communicates with an external device 404 and an external device 406. In this example, the passive LC resonant circuit is excited by RF signals 422 generated by the external device 404, and resulting oscillating signals in the excited LC resonant circuit may be received by the external device 404. In addition, the device 402 communicates with the external device 406 (e.g., programmer, a home monitor, etc.) to, for example, upload and download information. The external device 404 may collect measurements related to the resonant behavior of the LC resonant circuit 408.

The device 402 includes an LC resonant circuit 408, a signal processing circuit 410 (having one or more processors), a memory circuit 412, and a battery circuit 414 that are electrically coupled with one another, if applicable. Several other circuits that would be included in the device 402 are not shown to reduce the complexity of FIG. 4. The external device 404 includes an antenna 416 (e.g., a coil) that may be much larger than an effective antenna (e.g., the coil of the inductive circuit) for the LC resonant circuit 408. For example, the antenna 416 may have dimensions of 12-20 centimeters in diameter while the coil of the inductive circuit may have dimensions of 3-4 millimeters in diameter. In this way, an RF circuit 420 of the external device 404 is able to more effectively couple relatively high frequency RF signals 422 through the tissue of a patient (not shown) to excite the LC resonant circuit 408. The frequency of RF signals 422 may be at or near the resonant frequency of the LC resonant circuit 408.

The device 402 also includes a telemetry circuit 424 and associated antenna 426 for communicating with the external device 406 via RF signals 428. For example, the external device 406 may communicate with the device 402 to initiate glucose sensing operations, to upload data generated by the glucose sensing operations, to control cardiac-related operations, and so on. Of note, the external device 406 may employ a smaller antenna (not shown) than the antenna 416 since less RF energy may be required to communicate with the device 402 than is required to excite the LC resonant circuit 408 due to the use of lower frequency RF signals for this communication.

FIG. 5 illustrates an embodiment of a system 500 where a leadless glucose sensing device 502 that is implanted in a patient (not shown) communicates with an external device 504. Similar to the device 402 of FIG. 4, the device 502 communicates with the external device 504 (e.g., programmer, a home monitor, etc.) to, for example, upload and download information. In addition, the device 502 includes an LC resonant circuit 506, a signal processing circuit 508, and a memory circuit 510 that are electrically coupled in a suitable manner. Several other circuits that would be included in the device 502 are not shown to reduce the complexity of FIG. 5.

The configuration of FIG. 5 may be employed in cases where the external device 504 also includes the capability to excite a passive LC resonant circuit glucose sensor of the device 502. For example, the external device 504 may include a communication circuit 512 that communicates via at least one antenna 514 with a telemetry circuit 516 of the device 502 (as represented by RF signals 518) and that excites the LC resonant circuit 506 via RF signals 520. The use of the single external device 504 for both operations is enabled based on the teachings herein because relative large reactive components may be employed for the LC resonant circuit 506. The configuration of FIG. 5 also may be employed in cases where the device 502 employs an active LC resonant circuit glucose sensor. In such a case, the communication circuit 512 would not transmit the RF signals 520 to excite the LC resonant circuit 506. Rather, the communication circuit 512 would simply communicate with the telemetry circuit 516 via RF signals 518.

Figure 6:
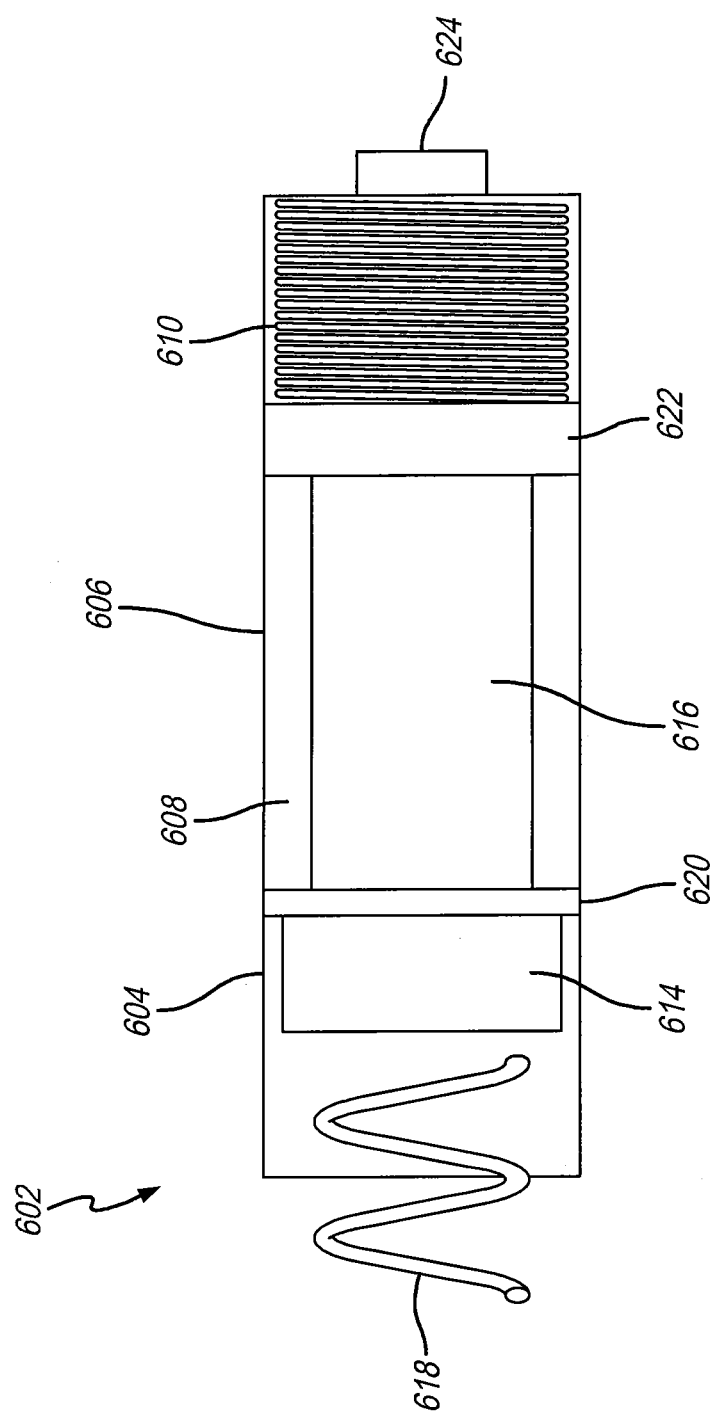
FIG. 6 illustrates a cross section of a leadless intra-cardiac medical device formed in accordance with an embodiment.

FIG. 6 illustrates a cross section of a leadless intra-cardiac medical device formed in accordance with an embodiment. The device 602 includes a housing 604 that houses LC-resonant circuit glucose sensing components and other cardiac-related components (e.g., for sensing and/or pacing). As discussed herein, an LC-resonant circuit includes a capacitive circuit (comprising plates 606 and a dielectric material 608) and an inductive circuit (comprising a multi-layer coil 610).

The plates 606 of the capacitive circuit take the form of a cylinder or a partial cylinder. Here, each cylinder is oriented in a longitudinal direction along the longitudinal axis of the housing 604. That is, the longitudinal axis of each cylinder is parallel with (or, in some cases, the same as) longitudinal axis of the housing 604.

In other embodiments (not shown in FIG. 6), the capacitive circuit may be housed entirely within (but located adjacent to) the housing 604. As shown in FIG. 6, the inductive circuit may take the form of a cylindrical coil or some other coil-like structure. The inductive circuit may be constructed in various ways. In some embodiments, the inductive circuit is constructed with DFT wire (41% AG or less) or copper wire. The wire may be coated with, for example, ETFE or some other insulation material. In some embodiments, the wire may be relatively thin (e.g., 100 micrometers to 2 mils) so that the coil may have large number of turns, thereby providing a higher value of inductance for a given size coil. The physical properties of the inductive circuit (e.g., the number of coil turns) and the capacitive circuit (e.g., size and distance between the plates 606) are selected to provide a desired resonant frequency for the LC resonant circuit. In some embodiments, the resonant circuit has a resonant frequency of 10 GHz or less.

The device 604 also includes a circuit 614 (e.g., comprising an integrated circuit and/or discrete circuits) for performing glucose sensing-related operations as taught herein. The circuit 614 is powered by a battery circuit 616. The device 604 also includes components for performing other cardiac-related operations. In this example, the device 602 includes electrodes 618, 620, 622, and 624. The circuit 614 also may include circuitry for acquiring and processing signals indicative of cardiac activity and for applying stimulation signals to cardiac tissue. For example, for sensing operations, at least one sensing circuit is coupled to one or more of the electrodes 618-624 for measuring cardiac electrical activity. In addition, for stimulation operations, at least one signal generator circuit is coupled to one or more of the electrodes 618-624 for stimulating cardiac tissue.

Electrodes of the device 602 may be configured in different ways for different stimulation operations. In some implementations, the electrode 618 acts as a cathode and the electrode 620 acts as an anode. In other implementations, the electrode 618 acts as the cathode and the housing 604 (e.g., comprising a conductive biocompatible material) acts as the anode.

Electrodes of the device 602 may be configured in different ways for different cardiac sensing operations. For example, in some implementations, the electrodes 618 and 620 are used for acquiring near-field signals, while the electrodes 622 and 624 are used for acquiring far-field signals. For sensing, the housing 604 (e.g., comprising a conductive material) and/or another electrode may act as a reference electrode (e.g., ground). As used herein, the term near-field signal refers to a signal that originates in a local chamber (i.e., the same chamber) where the corresponding sense electrodes are located. Conversely, the term far-field signal refers to a signal that originates in a chamber other than the local chamber where the corresponding sense electrodes are located.

To facilitate long-term implant within a patient, all external surfaces and materials of the leadless intra-cardiac medical device 602 comprise biocompatible materials. For example, the housing 604 may be constructed of titanium, a ceramic material, or some other suitable biocompatible material. The electrodes 618-624 may be constructed of titanium or some other suitable conductive and biocompatible material. In addition, the flexible material may be constructed of polyurethane, silicone or some other suitable flexible and biocompatible (and, optionally electrically insulating) material. Furthermore, in embodiments that employ insulators, the insulators may be constructed of ceramic, polyurethane, silicone or some other suitable electrically insulating and biocompatible material.

To facilitate long-term implant, the leadless intra-cardiac medical device 602 is hermetically sealed. To this end, hermetic sealing techniques may be employs to attach the flexible material 612 to the housing 604. In addition, hermetically sealed feedthroughs may be employed in some embodiments to electrically couple the electrodes 618-624 to internal conductors of the leadless intra-cardiac medical device 602. Alternatively, feedthroughs may not be employed in embodiments where the electrodes 618-624 are part of a hermetic housing 604. In such a case, an electrical connection may be made to an interior surface of these electrodes.

In some embodiments, the leadless intra-cardiac medical device 602 is sized to facilitate venous-based implant to a single cardiac chamber (e.g., the RV). For example, the housing 604 may have a cross-sectional width (e.g., outer diameter) of 12 French or less in some embodiments. In addition, to accommodate the internal circuitry (in particular, the battery of the battery circuit 616), the housing 604 may have a length of at least 30 millimeters in some embodiments. It should be appreciated; however, that different dimension may be employed in other embodiments. For example, the outer diameter of the housing 604 may be 7 or 8 French of less in some embodiments. Also, the length of the housing 604 may be 30 millimeters or less in some embodiments.

Figure 7:
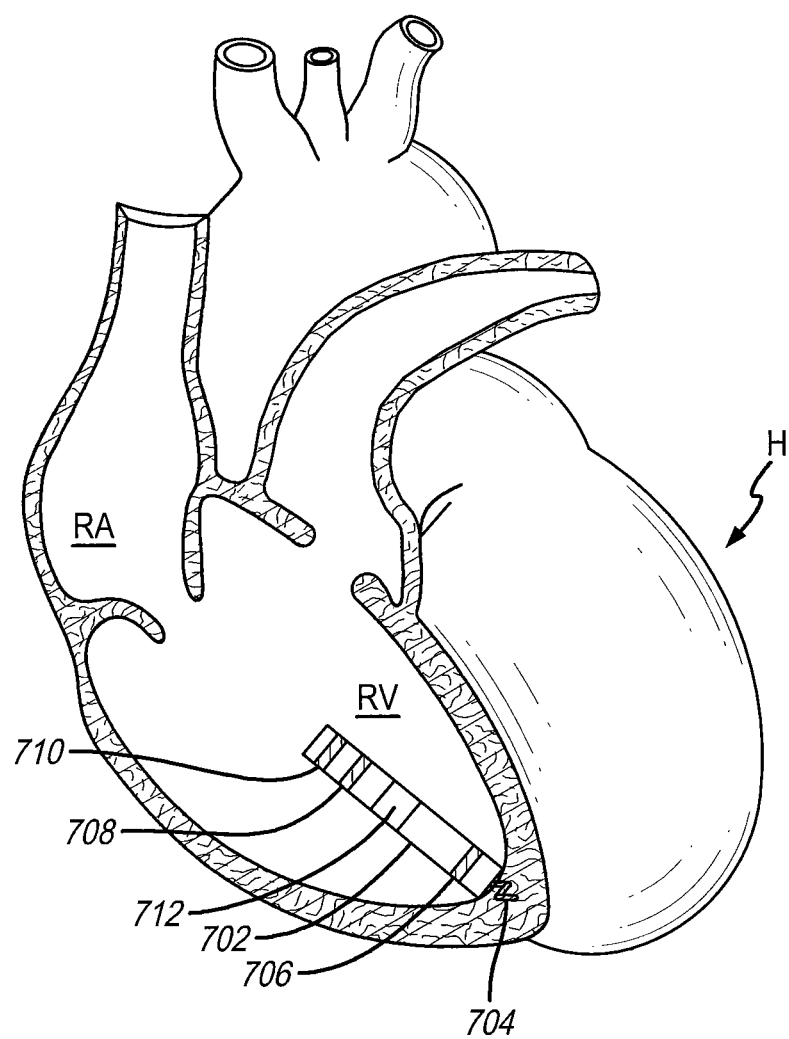
FIG. 7 illustrates an example of how a leadless intra-cardiac medical device may be implanted in a chamber of a heart H.

FIG. 7 illustrates an example of how a leadless intra-cardiac medical device 702 may be implanted in a chamber of a heart H. In this example, the leadless intra-cardiac medical device 702 is implanted at the apex of the right ventricle (RV) of the heart H. In accordance with the teachings herein, the device 702 includes an LC resonant circuit glucose sensor 712 for measure RV glucose.

A distal section of the leadless intra-cardiac medical device 702 comprises a helix electrode 704 that is actively affixed to an inner wall of the RV. The helix electrode 704 in combination with a ring electrode 706 may be used for near-field sensing of RV events. In addition, bipolar electrodes 708 and 710 at a proximal section of the leadless intra-cardiac medical device 702 may be employed for far-field sensing of RA events and/or other cardiac events. Here, the electrodes 708 and 710 may be optimized for such far-field sensing based on, for example, one or more of: placement of the electrodes 708 and 710 at a proximal section of the leadless intra-cardiac medical device 702, increased spacing between the electrodes 708 and 710, or increased sizing of the electrodes 708 and 710.

Figure 8A:
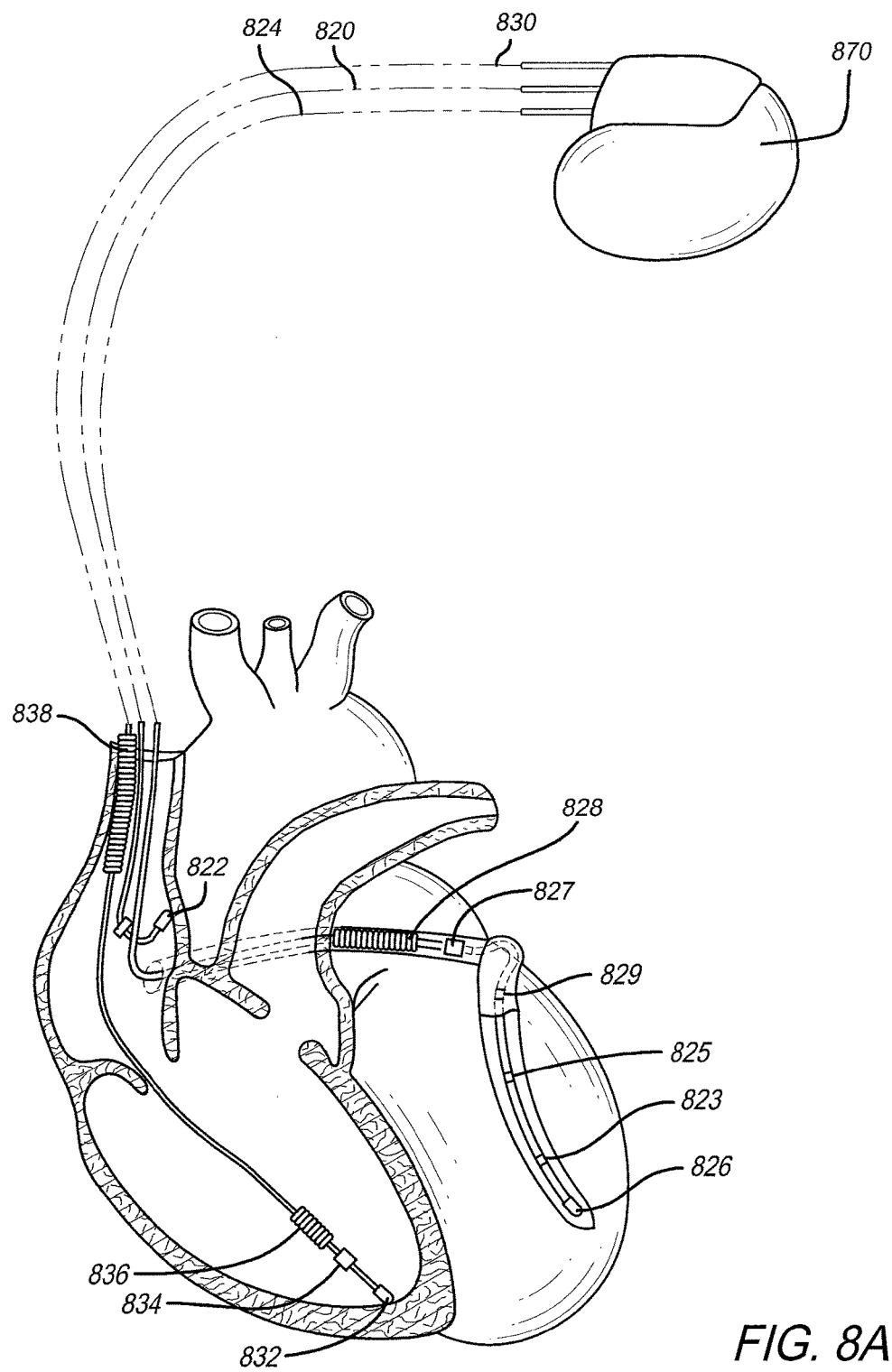
FIG. 8A illustrates an implantable medical device coupled to at least three leads implanted in or proximate a patient's heart for delivering multi-chamber stimulation according to an embodiment.

FIG. 8A illustrates a simplified diagram of an implantable medical device 870 in electrical communication with at least three leads 820, 824 and 830 implanted in or proximate a patient's heart 12 for delivering multi-chamber stimulation (e.g. pacing, ATP therapy, high voltage shocks and the like) according to an embodiment. The stimulation includes defibrillation shocks that are delivered along one or more defibrillation shocking vectors, such as between an RV electrode and a CAN electrode or between RV, SVC and CAN electrodes. The device 870 is also configured to perform ULV based estimation of the DFT based on local conduction information collected along a defibrillation vector and utilizing LV electrodes. As explained below, the leads 820, 824 and 830 are used to sense VT and VF and to deliver, among other things, antitachycardia and defibrillation shocks. The device 870 is programmable, by an operator, to set certain operating parameters, as well as therapy-related parameters. The device 870 is configured to operate with various configurations of leads. Exemplary lead configurations are shown in the Figures. The device 870 is configured to deliver various types of therapies.

To sense atrial cardiac signals and to provide right atrial chamber stimulation therapy, the medical device 870 is coupled to an implantable right atrial lead 820 having at least an atrial tip electrode 822, which typically is implanted in the patient's right atrial appendage. The implantable medical device 870 may be a pacing device, a pacing apparatus, a cardiac rhythm management device, an implantable cardiac stimulation device, an implantable cardioverter/defibrillator (ICD) and/or a cardiac resynchronization therapy (CRT) device.

To sense left atrial and ventricular cardiac signals and to provide left chamber pacing therapy, the medical device 870 is coupled to an LV lead 824. The LV lead 824 may receive atrial and ventricular cardiac signals and deliver left ventricular pacing therapy using a left ventricular (LV) tip electrode 826, and intermediate LV electrodes 823, 825 and 829. Left atrial pacing therapy uses, for example, first and second left atrial (LA) electrodes 827 and 828. The LV and LA electrodes 823-29 may represent sensing sites, where cardiac signals are sensed, and/or may represent pacing and/or shock therapy sites. A right ventricular lead 830 includes an RV tip electrode 832, an RV ring electrode 834, an RV coil electrode 836, and a superior vena cava (SVC) coil electrode 838 (also known as a RA coil electrode). The right ventricular lead 830 is capable of sensing cardiac signals, and delivering stimulation in the form of pacing and shock therapy to the SVC and/or right ventricle.

Figure 8B:
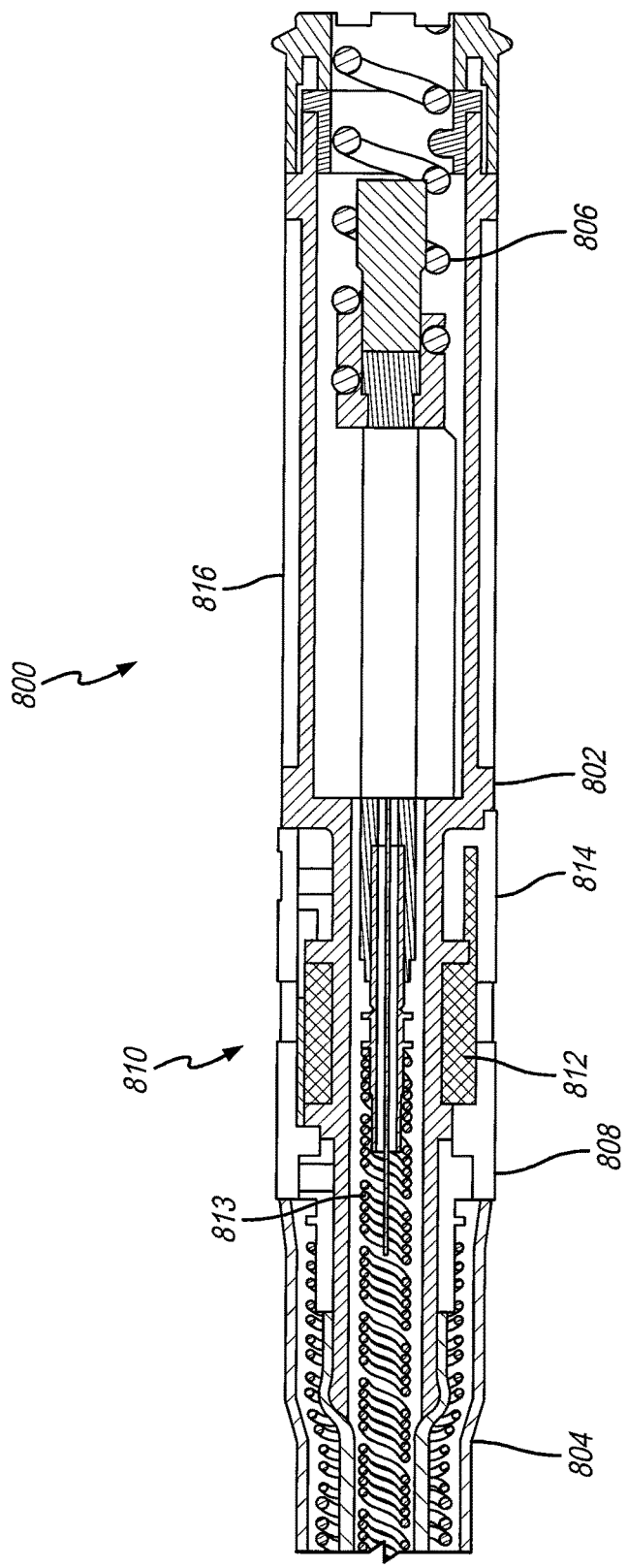
FIG. 8B illustrates a cross section of a portion of a lead configured to be implanted into a chamber of the heart.

FIG. 8B illustrates a cross section of a portion of one or more of the leads 820, 824 and 830 in FIG. 8A configured to be implanted into a chamber of the heart. A proximal end of the lead is connected to the IMD 870. The lead 800 includes a lead body 802 extending along a length of the lead 800. The lead body 802 includes one or more lumen that are configured to receive corresponding conductors (for example helical conductor 804 and 806) that electrically connect one or more electrodes 808 on the lead 800 to an IMD (not shown) which may be located proximate to the heart (such as in a sub clavicle pocket). In the example of FIG. 8, the electrode 808 represents a ring electrode, although it is understood that other types of electrodes may be provided within the illustrated portion of the lead 800, as well as at other locations along the length thereof.

The lead 800 includes an LC resonant circuit 810 that includes an inductive circuit and a capacitive circuit. The inductive circuit comprises one or more inductor coils 812 wound about a central lumen 813. The capacitive circuit comprises conductive plates 814 and 816. The inductive and capacitive circuits are electrically coupled to one another, in series or parallel. Additionally, or alternatively, the capacitive circuit 162 (FIG. 1B) or 190 (FIG. 1E) or another may be used.

Optionally, a second LC resonant circuit may be provided on the lead 800, where the second LC resonant circuit is constructed to exhibit a resonant frequency that varies in response to pressure changes. In this alternative embodiment, one LC resonant circuit is set to have a resonant frequency sensitive to glucose changes in the blood, while the other LC resonant circuit is configured to have a resonant frequency that varies with pressure change in the surrounding area. The first and second LC resonant circuits have separate and distinct resonant frequencies. As one example, the inductance value for the second LC resonant circuit (responsive to pressure change) may be larger than the inductance value of the LC resonant circuit responsive to glucose concentration.

Representative operations relating to glucose sensing by an embodiment of a leadless intra-cardiac medical device in accordance with the teachings herein will be described in more detail in conjunction with the flowchart of FIG. 10. For convenience, the operations of FIG. 10 (or any other operations discussed or taught herein) may be described as being performed by specific components. It should be appreciated, however, that these operations may be performed by other types of components and may be performed using a different number of components. It also should be appreciated that one or more of the operations described herein may not be employed in a given implementation.

Figure 9:
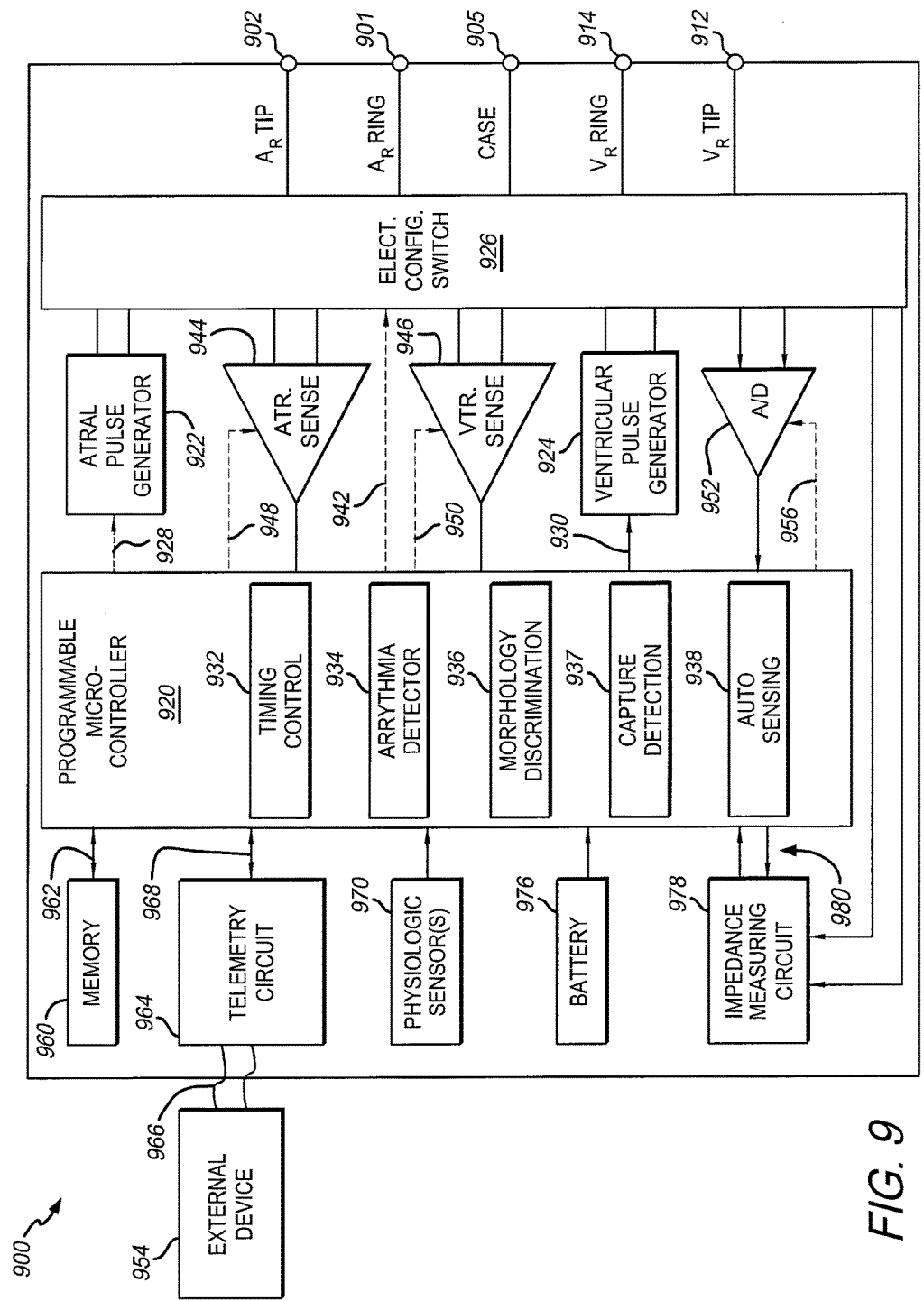
FIG. 9 illustrates sample components of an implantable leadless intra-cardiac medical device in accordance with embodiments herein.

FIG. 9 illustrates sample components of an embodiment of an implantable leadless intra-cardiac medical device 900 (e.g., a stimulation device such as an implantable cardioverter defibrillator, a pacemaker, etc., or a monitoring device) that may be configured in accordance with the various embodiments that are described herein. It is to be appreciated and understood that other cardiac devices can be used and that the description below is given, in its specific context to assist the reader in understanding, with more clarity, the embodiments described herein.

In various embodiments, the device 900 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation. A housing 905 for the device 900 is often referred to as the "can", "case" or "case electrode", and may be programmably selected to act as the return electrode for all "unipolar" modes. The housing 905 may further be used as a return electrode alone or in combination with one or more coil electrodes (not shown) for shocking purposes. As discussed herein, the housing 905 may be constructed of a biocompatible material (e.g., titanium) to facilitate implant within a patient.

The device 900 further includes a plurality of terminals that connect the internal circuitry of the device 900 to electrodes 901, 902, 912, and 914 of the device 900. Here, the name of the electrodes to which each terminal is connected is shown next to that terminal. The device 900 may be configured to include various other terminals depending on the requirements of a given application. Thus, it should be appreciated that other terminals (and associated circuitry) may be employed in other embodiments.

To achieve right atrial sensing and pacing, a right atrial tip terminal (A.sub.R TIP) is adapted for connection to a right atrial tip electrode 902. A right atrial ring terminal (A.sub.R RING) may also be included and adapted for connection to a right atrial ring electrode 901. To achieve right ventricular sensing and pacing, a right ventricular tip terminal (V.sub.R TIP) and a right ventricular ring terminal (V.sub.R RING) are adapted for connection to a right ventricular tip electrode 912 and a right ventricular ring electrode 914, respectively.

At the core of the device 900 is a programmable microcontroller 920 that controls the various modes of stimulation therapy. As is well known in the art, microcontroller 920 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 920 includes the ability to process or monitor input signals (data or information) as controlled by a program code stored in a designated block of memory. The type of microcontroller is not critical to the described implementations. Rather, any suitable microcontroller 920 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 9 also shows an atrial pulse generator 922 and a ventricular pulse generator 924 that generate pacing stimulation pulses for delivery by the right atrial electrodes, the right ventricular electrode, or some combination of these electrodes via an electrode configuration switch 926. It is understood that in order to provide stimulation therapy in each of the four chambers of the heart, the atrial and ventricular pulse generators 922 and 924 may include dedicated, independent pulse generators, multiplexed pulse generators, or shared pulse generators. The pulse generators 922 and 924 are controlled by the microcontroller 920 via appropriate control signals 928 and 930, respectively, to trigger or inhibit the stimulation pulses.

Microcontroller 920 further includes timing control circuitry 932 to control the timing of the stimulation pulses (e.g., pacing rate, atrioventricular (AV) delay, inter-atrial conduction (A-A) delay, or inter-ventricular conduction (V-V) delay, etc.) or other operations, as well as to keep track of the timing of refractory periods, blanking intervals, noise detection windows, evoked response windows, alert intervals, marker channel timing, etc., as known in the art.

Microcontroller 920 further includes an arrhythmia detector 934. The arrhythmia detector 934 may be utilized by the device 900 for determining desirable times to administer various therapies. The arrhythmia detector 934 may be implemented, for example, in hardware as part of the microcontroller 920, or as software/firmware instructions programmed into the device 900 and executed on the microcontroller 920 during certain modes of operation.

Microcontroller 920 may include a morphology discrimination module 936, a capture detection module 937 and an auto sensing module 938. These modules are optionally used to implement various exemplary recognition algorithms or methods. The aforementioned components may be implemented, for example, in hardware as part of the microcontroller 920, or as software/firmware instructions programmed into the device 900 and executed on the microcontroller 920 during certain modes of operation.

The electrode configuration switch 926 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 926, in response to a control signal 942 from the microcontroller 920, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 944 and ventricular sensing circuits (VTR. SENSE) 946 may also be selectively coupled to the right atrial electrodes and the right ventricular electrodes through the switch 926 for detecting the presence of cardiac activity in each of the four chambers of the heart. Accordingly, the atrial and ventricular sensing circuits 944 and 946 may include dedicated sense amplifiers, multiplexed amplifiers, or shared amplifiers. Switch 926 determines the "sensing polarity" of the cardiac signal by selectively closing the appropriate switches, as is also known in the art. In this way, the clinician may program the sensing polarity independent of the stimulation polarity. The sensing circuits (e.g., circuits 944 and 946) are optionally capable of obtaining information indicative of tissue capture.

Each sensing circuit 944 and 946 preferably employs one or more low power, precision amplifiers with programmable gain, automatic gain control, bandpass filtering, a threshold detection circuit, or some combination of these components, to selectively sense the cardiac signal of interest. The automatic gain control enables the device 900 to deal effectively with the difficult problem of sensing the low amplitude signal characteristics of atrial or ventricular fibrillation.

The outputs of the atrial and ventricular sensing circuits 944 and 946 are connected to the microcontroller 920, which, in turn, is able to trigger or inhibit the atrial and ventricular pulse generators 922 and 924, respectively, in a demand fashion in response to the absence or presence of cardiac activity in the appropriate chambers of the heart. Furthermore, as described herein, the microcontroller 920 is also capable of analyzing information output from the sensing circuits 944 and 946, a data acquisition system 952, or both. This information may be used to determine or detect whether and to what degree tissue capture has occurred and to program a pulse, or pulses, in response to such determinations. The sensing circuits 944 and 946, in turn, receive control signals over signal lines 948 and 950, respectively, from the microcontroller 920 for purposes of controlling the gain, threshold, polarization charge removal circuitry (not shown), and the timing of any blocking circuitry (not shown) coupled to the inputs of the sensing circuits 944 and 946 as is known in the art.

For arrhythmia detection, the device 900 utilizes the atrial and ventricular sensing circuits 944 and 946 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 934 of the microcontroller 920 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 952. The data acquisition system 952 is configured (e.g., via signal line 956) to acquire intra-cardiac electrogram ("IEGM") signals or other signals, convert the raw analog data into a digital signal, and store the digital signals for later processing, for telemetric transmission to an external device 954, or both. For example, the data acquisition system 952 may be coupled to the right atrial electrodes and the right ventricular electrodes through the switch 926 to sample cardiac signals across any pair of desired electrodes.

The data acquisition system 952 also may be coupled to receive signals from other input devices. For example, the data acquisition system 952 may sample signals from a physiologic sensor 970 or other components shown in FIG. 9 (connections not shown).

The microcontroller 920 is further coupled to a memory 960 by a suitable data/address bus 962, wherein the programmable operating parameters used by the microcontroller 920 are stored and modified, as required, in order to customize the operation of the device 900 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 952), which data may then be used for subsequent analysis to guide the programming of the device 900.

Advantageously, the operating parameters of the implantable device 900 may be non-invasively programmed into the memory 960 through a telemetry circuit 964 in telemetric communication via communication link 966 with the external device 954, such as a programmer, transtelephonic transceiver, a diagnostic system analyzer or some other device. The microcontroller 920 activates the telemetry circuit 964 with a control signal (e.g., via bus 968). The telemetry circuit 964 advantageously allows intra-cardiac electrograms and status information relating to the operation of the device 900 (as contained in the microcontroller 920 or memory 960) to be sent to the external device 954 through an established communication link 966.

The device 900 includes one or more physiologic sensors 970. At least one sensor 970 comprises a glucose sensor as taught herein. In some embodiments, the device 900 may include a "rate-responsive" sensor that may provide, for example, information to aid in adjustment of pacing stimulation rate according to the exercise state of the patient. One or more physiologic sensors 970 (e.g., a glucose sensor) may be used to detect changes in cardiac output, changes in the physiological condition of the heart, or diurnal changes in activity (e.g., detecting sleep and wake states). Accordingly, the microcontroller 920 may respond to this sensing by adjusting the various pacing parameters (such as rate, A-V Delay, V-V Delay, etc.) at which the atrial and ventricular pulse generators 922 and 924 generate stimulation pulses.

While shown as being included within the device 900, it is to be understood that a physiologic sensor 970 may also be external to the device 900, yet still be implanted within or carried by the patient. Examples of physiologic sensors that may be implemented in conjunction with the device 900 include sensors that sense respiration rate, pH of blood, ventricular gradient, oxygen saturation, blood glucose and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 970 may optionally include one or more of components to help detect movement (via, e.g., a position sensor or an accelerometer) and minute ventilation (via an MV sensor) in the patient. Signals generated by the position sensor and MV sensor may be passed to the microcontroller 920 for analysis in determining whether to adjust the pacing rate, etc. The microcontroller 920 may thus monitor the signals for indications of the patient's position and activity status, such as whether the patient is climbing up stairs or descending down stairs or whether the patient is sitting up after lying down.

The device 900 additionally includes a battery 976 that provides operating power to all of the circuits shown in FIG. 9. For a device 900 which employs shocking therapy, the battery 976 is capable of operating at low current drains (e.g., preferably less than 10 .mu.A) for long periods of time, and is capable of providing high-current pulses (for capacitor charging) when the patient requires a shock pulse (e.g., preferably, in excess of 2 A, at voltages above 200 V, for periods of 10 seconds or more). The battery 976 also desirably has a predictable discharge characteristic so that elective replacement time can be detected. Accordingly, the device 900 preferably employs lithium or other suitable battery technology.

The device 900 can further include magnet detection circuitry (not shown), coupled to the microcontroller 920, to detect when a magnet is placed over the device 900. A magnet may be used by a clinician to perform various test functions of the device 900 and to signal the microcontroller 920 that the external device 954 is in place to receive data from or transmit data to the microcontroller 920 through the telemetry circuit 964.

The device 900 further includes an impedance measuring circuit 978 that is enabled by the microcontroller 920 via a control signal 980. The known uses for an impedance measuring circuit 978 include, but are not limited to, electrode impedance surveillance during the acute and chronic phases for proper performance, electrode positioning or dislodgement; detecting operable electrodes and automatically switching to an operable pair if dislodgement occurs; measuring respiration or minute ventilation; measuring thoracic impedance for determining shock thresholds; detecting when the device 900 has been implanted; measuring stroke volume; and detecting the opening of heart valves, etc. The impedance measuring circuit 978 is advantageously coupled to the switch 926 so that any desired electrode may be used.

In the case where the device 900 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 920 may include a shocking circuit (not shown). The shocking circuit generates shocking pulses of low (e.g., up to 0.5 J), moderate (e.g., 0.5 J to 10 J), or high energy (e.g., 11 J to 40 J), as controlled by the microcontroller 920. Such shocking pulses may be applied to the patient's heart H through, for example, two or more shocking electrodes (not shown).

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 920 is capable of controlling the synchronous or asynchronous delivery of the shocking pulses.

The device 900 thus illustrates several components that may provide the implantable intra-cardiac medical device functionality described above. For example, the microcontroller 920 may control and perform the operations of FIGS. 2B and 2C. The microcontroller 920 is configured to collect measurements indicative of the resonant frequency of the LC resonant circuit; and calculate data indicative of a glucose level of the blood based on the measurements indicative of the resonant frequency. The microcontroller is further configured to repeat the collecting and calculating operations during at least first and second test intervals, and to determine whether the glucose level changes between the first and second test intervals. For example, the microcontroller 920 (e.g., a processor providing signal processing functionality) may implement or support at least a portion of the processing functionality discussed above. Also, one or more of the switch 926, the sense circuits 944, 946, and the data acquisition system 952 may acquire cardiac signals that are used in the signal acquisition operations discussed above. Similarly, one or more of the switch 926 and the pulse generator circuits 922, 924 may be used to provide stimulation signals that are used in the cardiac stimulation operations discussed above. The data described above (e.g., glucose data and/or cardiac data) may be stored in the data memory 960. The physiologic sensors 970 may comprise the glucose sensor(s) discussed above. Thus, in general, the processing circuitry described herein (e.g., the circuit 208, 308, or 614, etc.) may correspond to one or more of the illustrated components of the device 900.

Figure 10:
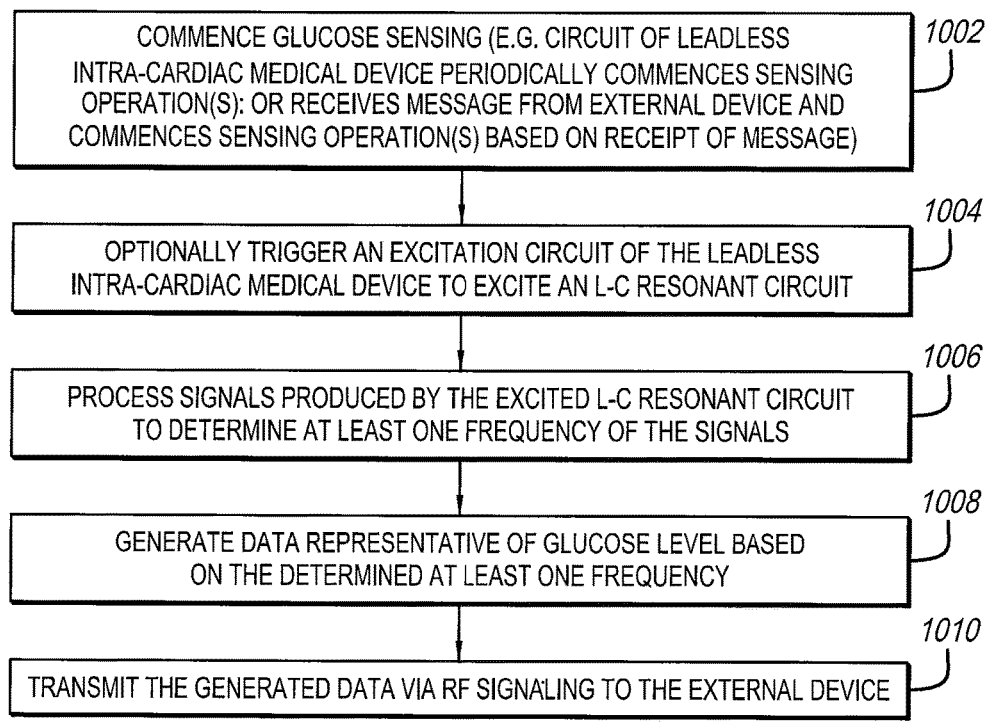
FIG. 10 illustrates a process for measuring glucose concentration.

FIG. 10 illustrates a process for measuring glucose concentration. As represented by block 1002 of FIG. 10, at some point in time, the leadless intra-cardiac medical device commences glucose sensing. For example, the device may receive a message (e.g., a command from an external monitor device) or some other type of signal (e.g., an RF signal from an external device that provides an RF excitation signal) from an external device. As a result of the receipt of the message or signal, the leadless intra-cardiac medical device may commence processing the oscillating signal from the LC resonant circuit and generating data representative of glucose levels. As another example, the leadless intra-cardiac medical device may be configured to periodically conduct glucose sensing operations.

As represented by block 1004, in embodiments where the leadless intra-cardiac medical device comprises an active LC resonant circuit, the device may trigger an excitation circuit to excite the LC resonant circuit. As discussed herein, this trigger may be based on receipt of a message or signal, based on a glucose sensing schedule (e.g., periodic sensing) implemented at the device, or based on some other factor(s).

As represented by block 1006, the leadless intra-cardiac medical device processes signal produced by the excited LC resonant circuit to determine at least one frequency of the signals. For example, the device may monitor the frequency of the signals over a period of time to determine how the frequency varies over that period of time.

As represented by block 1008, the leadless intra-cardiac medical device generates data representative of the glucose level based on the at least one frequency determined at block 1006. For example, the device may generate data indicative of how the measured cardiac glucose varies over a designated period of time.

As represented by block 1010, the leadless intra-cardiac medical device transmits the data generated at block 1008 to an external device (e.g., an external monitoring device) via RF signaling. For example, the leadless intra-cardiac medical device may send this information on-demand (e.g., in response to a message), according to a schedule (e.g., periodically), or in some other suitable manner.

Figure 11:
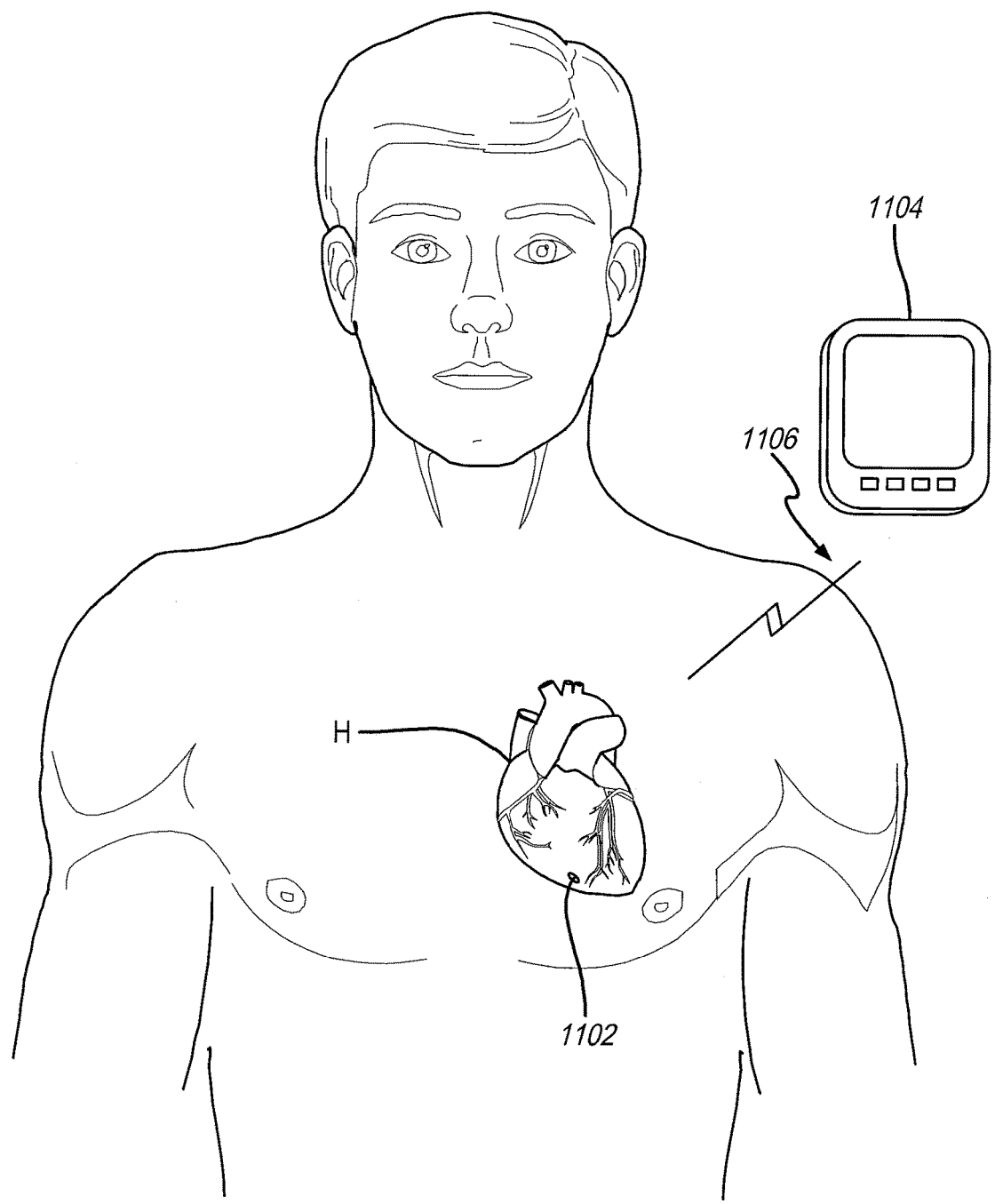
FIG. 11 is a simplified diagram of a glucose sensing device that communicates with a device that is located external to the patient P.

FIG. 11 is a simplified diagram of a device 1102 (implanted within a patient P) that communicates with a device 1104 that is located external to the patient P. The implanted device 1102 and the external device 1104 communicate with one another via a wireless communication link 1106 (as represented by the depicted wireless symbol).

In the illustrated example, the implanted device 1102 is a leadless intra-cardiac medical device including an LC resonant circuit glucose sensor (not shown) in accordance with the teachings herein. For example, the implanted device 1102 may be a pacemaker, an implantable cardioverter defibrillator, or some other similar device. It should be appreciated, however, that the implanted device 1102 may take other forms.

The external device 1104 also may take various forms. For example, the external device 1104 may be a base station, a programmer, a home safety monitor, a personal monitor, a follow-up monitor, a wearable monitor, or some other type of device that is configured to communicate with the implanted device 1102. The communication link 1106 may be used to transfer information between the devices 1102 and 1104 in conjunction with various applications such as remote home-monitoring, clinical visits, data acquisition, remote follow-up, and portable or wearable patient monitoring/control systems. For example, when information needs to be transferred between the devices 1102 and 1104, the patient P moves into a position that is relatively close to the external device 1104, or vice versa.

The external device 1104 may send information it receives from an implanted device to another device (e.g., that may provide a more convenient means for a physician to review the information). For example, the external device 1104 may send the information to a web server (not shown). In this way, the physician may remotely access the information (e.g., by accessing a website). The physician may then review the information uploaded from the implantable device to determine whether medical intervention is warranted.

It should be appreciated that various modifications may be incorporated into the disclosed embodiments based on the teachings herein. For example, the structure and functionality taught herein may be incorporated into types of devices other than the specific types of devices described above. In addition, glucose sensors for a leadless intra-cardiac medical device may be implemented in different ways in different embodiments based on the teachings herein. Different types of structural members and mechanical support structures may be employed in conjunction with a leadless intra-cardiac medical device as taught herein. Also, various algorithms or techniques may be employed to monitor glucose in various cardiac chambers (e.g., RA, RV, LA, and LV chambers) in accordance with the teachings herein. In some aspects, an apparatus or any component of an apparatus may be configured to provide functionality as taught herein by, for example, manufacturing (e.g., fabricating) the apparatus or component so that it will provide the functionality, by programming the apparatus or component so that it will provide the functionality, or through the use of some other suitable means.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may send raw data or processed data to an external device that then performs the necessary processing.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above, it will be understood that the teachings herein are intended to cover any changes, adaptations or modifications that are within the scope of the disclosure.

The (module/controller) may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the (module/controller) represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The (module/controller) may execute a set of instructions that are stored in one or more storage elements, in order to process data. The storage elements may also store data or other information as desired or needed. The storage element may be in the form of an information source or a physical memory element within the (module/controller) The set of instructions may include various commands that instruct the (module/controller) to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A blood glucose sensing device, comprising:
   a housing comprising an exterior surface and defining an interior space, the housing configured to be located within a cardiovascular pathway of a patient; and
   an inductor-capacitor (LC) circuit located within the interior space defined by the housing, wherein the inductor-capacitor circuit comprises an inductive circuit and a capacitive circuit electrically coupled to one another; and
   the inductive and capacitive circuits having inductance and capacitance values that define a blood glucose sensitive resonant frequency such that a resonant frequency of the LC resonant circuit varies in response to changes in blood glucose levels within the blood in the cardiovascular pathway surrounding the housing.

2. The device of claim 1, further comprising a microprocessor configured to process signals received from the LC resonant circuit to generate data representative of the blood glucose level.

3. The device of claim 2, wherein the microprocessor processes the signals from the LC resonant circuit to determine the resonant frequency of the LC resonant circuit; and based on the resonant frequency, determines the blood glucose level.

4. The device of claim 2, further comprising an implantable medical device (IMD) coupled to a proximal end of a lead, the IMD including the microprocessor, the lead having a distal end configured to be implanted within a heart of the patient, the LC resonant circuit located within the lead proximate to the distal end such that the LC resonant circuit is located within a chamber of the heart.

5. The device of claim 1, wherein the LC circuit includes capacitor plates that form an electrical field having fringe flex components projecting from ends of the plates into the blood pool to be sensitivity to permittivity changes in the blood pool.

6. The device of claim 1, wherein the LC resonant circuit comprises curved capacitor plates arranged to face one another with ends of the plates adjacent to one another.

7. The device of claim 1, further comprising a microcontroller configured to build a model of a relation between resonant frequencies, and permittivities.

8. The device of claim 1, further comprising a microcontroller configured to:
   collect measurements indicative of the resonant frequency of the LC resonant circuit; and
   calculate data indicative of a glucose level of the blood based on the measurements indicative of the resonant frequency.

9. The device of claim 8, wherein the microcontroller is further configured to repeat the collecting and calculating operations during at least first and second test intervals, and to determine whether the glucose level changes between the first and second test intervals.

10. A method, comprising:
    implanting a blood glucose sensing device within a cardiovascular pathway of a patient, the sensing device including an inductor-capacitor (LC) circuit that has a blood glucose sensitive resonant frequency that varies in response to changes in blood glucose levels of the blood; and
    generating an excitation signal to excite the LC resonant circuit; and
    collecting measurements indicative of the resonant frequency of the LC resonant circuit; and
    calculating data indicative of a glucose level of the blood based on the measurements indicative of the resonant frequency.

11. The method of claim 10, wherein the generating, collecting and calculating operations are repeated during at least first and second test intervals, the method further comprising determining whether the glucose level changes between the first and second test intervals.

12. The method of claim 10, further comprising calculating a permittivity of the blood based on the measurements and identifying a change in the glucose level based on a change in the permittivity of the blood over time.

13. The method of claim 12, wherein the calculating operation includes comparing the change in the permittivity to a threshold, and wherein the identifying operation identifies that the glucose level has changed when the change in permittivity exceeds the threshold.

14. The method of claim 10, further comprising determining the resonant frequency based on the measurements and determining a permittivity of the blood proximate to the LC resonant circuit based on the resonant frequency.

15. The method of claim 10, wherein the generating operation includes generating the excitation signal from an external source outside of the patient.

16. The method of claim 10, wherein the generating operation includes generating the excitation signal from an implantable device within the patient.

17. The method of claim 16, wherein the implantable device includes the blood glucose sensing device.

* * * * *